(12) United States Patent
Dillon et al.

(10) Patent No.: US 11,234,798 B2
(45) Date of Patent: *Feb. 1, 2022

(54) SCANNING SEQUENCE FOR AN INTRA-ORAL IMAGING SYSTEM

(71) Applicant: ORMCO CORPORATION, Orange, CA (US)

(72) Inventors: Robert F. Dillon, Bedford, NH (US); Craig A. Andreiko; Andrew F. Vesper, Townsend, MA (US); Neil H. K. Judell, Cambridge, MA (US); Timothy I. Fillion, Bedford, MA (US)

(73) Assignee: ORMCO CORPORATION, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/160,230

(22) Filed: Oct. 15, 2018

(65) Prior Publication Data

US 2019/0046304 A1 Feb. 14, 2019

Related U.S. Application Data

(63) Continuation of application No. 14/209,648, filed on Mar. 13, 2014, now Pat. No. 10,098,713.

(60) Provisional application No. 61/784,535, filed on Mar. 14, 2013.

(51) Int. Cl.
*A61C 9/00* (2006.01)
*A61B 1/24* (2006.01)
*A61B 1/00* (2006.01)
*A61B 1/04* (2006.01)

(52) U.S. Cl.
CPC .......... *A61C 9/0053* (2013.01); *A61B 1/0002* (2013.01); *A61B 1/0005* (2013.01); *A61B 1/00009* (2013.01); *A61B 1/04* (2013.01); *A61B 1/24* (2013.01); *A61C 9/006* (2013.01)

(58) Field of Classification Search
None
See application file for complete search history.

(56) References Cited

U.S. PATENT DOCUMENTS

| | | | |
|---|---|---|---|
| 6,402,707 B1 | 6/2002 | Ernst | |
| 7,717,708 B2 | 5/2010 | Sachdeva et al. | |
| 7,905,725 B2 | 3/2011 | Chishti et al. | |
| 8,390,822 B2 | 3/2013 | Dillon et al. | |
| 2004/0265770 A1 | 12/2004 | Chapoulaud et al. | |
| 2005/0058962 A1 | 3/2005 | Siemons et al. | |
| 2012/0062557 A1 | 3/2012 | Dillon et al. | |
| 2012/0129119 A1 | 5/2012 | Oda | |
| 2013/0218530 A1* | 8/2013 | Deichmann | A61C 13/0004 703/1 |

* cited by examiner

*Primary Examiner* — Vikkram Bali
(74) *Attorney, Agent, or Firm* — Michael Best & Friedrich LLP

(57) ABSTRACT

Provided are a system, method, and computer readable storage medium for generating an intra-oral scan of a dentition. A contiguous scan of an occlusal surface of at least a part of one arch of the dentition is generated. At least one additional surface is associated to the contiguous scan of the occlusal surface.

20 Claims, 20 Drawing Sheets

SCANNING SEQUENCE FOR AN INTRA-ORAL IMAGING SYSTEM

RELATED APPLICATIONS

This application is a continuation of U.S. patent application Ser. No. 14/209,648, filed Mar. 13, 2014, entitled SCANNING SEQUENCE FOR AN INTRA-ORAL IMAGING SYSTEM, which claims the benefit of U.S. Provisional Patent Application No. 61/784,535, filed Mar. 14, 2013, the entire contents of both of which are incorporated herein by reference.

FIELD

The disclosure relates to a method, system, and computer readable storage medium for a scanning sequence for an intra-oral imaging system.

BACKGROUND

An intra-oral imaging system is a diagnostic equipment that allows a dental practitioner to see the inside of a patient's mouth and display the topographical characteristics of teeth on a display unit. Certain three-dimensional (3D) intra-oral imagers may be comprised of an intra-oral camera with a light source. The 3D intra-oral imager may be inserted into the oral cavity of a patient by a dental practitioner. After insertion of the intra-oral imager into the oral cavity, the dental practitioner may capture images of visible parts of the teeth and the gingivae. The 3D intra-oral imager may be fabricated in the form of a slender rod that is referred to as a wand or a handpiece. The wand may be approximately the size of a dental mirror with a handle that is used in dentistry. The wand may have a built-in light source and a video camera that may achieve an imaging magnification, ranging in scale from 1/10 to 40 times or more. This allows the dental practitioner to discover certain types of details and defects of the teeth and gums. The images captured by the intra-oral camera may be displayed on a display unit. Additionally, three-dimensional surfaces generated from images captured (i.e., scanned) by the intra-oral imaging system may be displayed on the display unit.

SUMMARY OF THE PREFERRED EMBODIMENTS

Provided are a system, method, and computer readable storage medium for generating an intra-oral scan of a dentition. A contiguous scan of an occlusal surface of at least a part of one arch of the dentition is generated. At least one additional surface is associated to the contiguous scan of the occlusal surface.

In additional embodiments, the at least one additional surface comprises a plurality of labial surfaces and a plurality of lingual surfaces.

In further embodiments, each scan of a labial or a lingual surface includes a part of the occlusal surface, where the part of the occlusal surface that is included in each scan of the labial or lingual surface is used to associate the labial or the lingual surface to the contiguous scan of the occlusal surface.

In yet further embodiments, each scan of the labial or the lingual surface is performed by moving a wand in a predetermined pattern.

In certain embodiments, the occlusal surface is imaged prior to the plurality of labial and lingual surfaces to display in real-time a three-dimensional representation of the dentition.

In additional embodiments, the occlusal surface is imaged in a single segment, where the plurality of labial surfaces and the plurality of lingual surfaces are each imaged in a plurality of segments.

In yet additional embodiments, selected frames of the contiguous scan of the occlusal surface that have an overlap based on an analysis of data, are matched to generate an occlusal backbone.

In further embodiments, the overlap is based on noise characteristics of the data.

In additional embodiments, to perform a real-time display of a three-dimensional representation of the dentition, a coarse matching is performed by matching features, prior to a three-dimensional reconstruction based on a point cloud alignment.

In further embodiments, the occlusal backbone is a first occlusal backbone, and other frames that are different from the selected frames are linked to the occlusal backbone to generate a second occlusal backbone that is more accurate than the first occlusal backbone.

In certain embodiments, areas representing at least one of a tongue, a cheek, and a lip, are removed from the second occlusal backbone to generate a third occlusal backbone.

In further embodiments, the areas representing at least one of the tongue, the cheek, and the lip, are removed from the second occlusal backbone, based on differences in surface normals, color, or rigidity properties.

In additional embodiments, interferometric fringes are projected on the occlusal surface primarily along an anterior-posterior direction.

Provided also is an imaging system that comprises a projector that projects interferometric fringes on an occlusal surface of at least a part of one arch of a dentition primarily along an anterior-posterior direction, and an imaging sensor that is used to view the interferometric fringes.

In certain embodiments, the imaging system is configured to generate a contiguous scan of an occlusal surface, and associate at least one additional surface to the contiguous scan of the occlusal surface. In further embodiments, the at least one additional surface comprises a plurality of labial surfaces and a plurality of lingual surfaces.

BRIEF DESCRIPTION OF THE DRAWINGS

Referring now to the drawings in which like reference numbers represent corresponding parts throughout.

DETAILED DESCRIPTION

In the following description, reference is made to the accompanying drawings which form a part hereof and which illustrate several embodiments. It is understood that other embodiments may be utilized and structural and operational changes may be made.

Using an Intra-Oral Imaging System for Scanning a Dental Arch

A dental practitioner may insert a wand of the intra-oral imaging system into a patient's oral cavity to acquire images of the patient's teeth. In certain embodiments, the dental practitioner first acquires an occlusal scan of the patient's teeth in a single segment via an uninterrupted motion of the wand over the occlusal surface of the teeth. While performing the occlusal scan the wand may rest on the teeth and glide smoothly over the dental arch.

Subsequent to performing the occlusal scan, the dental practitioner may use the wand to acquire images of each of the lingual and labial surfaces of the dental arch in a plurality of segments. The presence of lips, tongue, cheek, etc., makes it difficult to acquire images of the lingual and labial surface via an uninterrupted motion of the wand and therefore each of the lingual and labial surfaces are imaged in multiple segments.

In certain embodiments, the frames of the occlusal scan are merged into an occlusal backbone to which the segments of the lingual and labial surfaces are linked to generate a three-dimensional surface of the dental arch that is displayed in real-time on a display device.

The occlusal backbone is generated in multiple phases. In a first phase, in order to statistically limit the effect of random noise and other image characteristics, selected frames that overlap by about 50% (or some other percentage) are stitched to form a rough occlusal backbone and then other frames are stitched to the rough occlusal backbone. Subsequently, areas representing tongue, cheek, and lips are removed from the occlusal backbone, and a restitching of frames is performed to generate a more accurate occlusal backbone. The segments of lingual and labial surfaces are then acquired by moving the wand in an exemplary pattern, such as, in the pattern of a hook. In each segment of the lingual and labial surface that is acquired, the movement of the wand in the exemplary pattern ensures that part of the occlusal scan is also acquired. The part of the occlusal scan that is acquired is used to match the segments of the lingual and labial surfaces to the occlusal backbone, and the three-dimensional surface of the dental arch is displayed on the display device.

The embodiments allow generation of a more accurate three-dimensional surface of the dental arch for real-time display, in comparison to situations in which a contiguous occlusal scan is not used.

EXEMPLARY EMBODIMENTS

Figure 1:
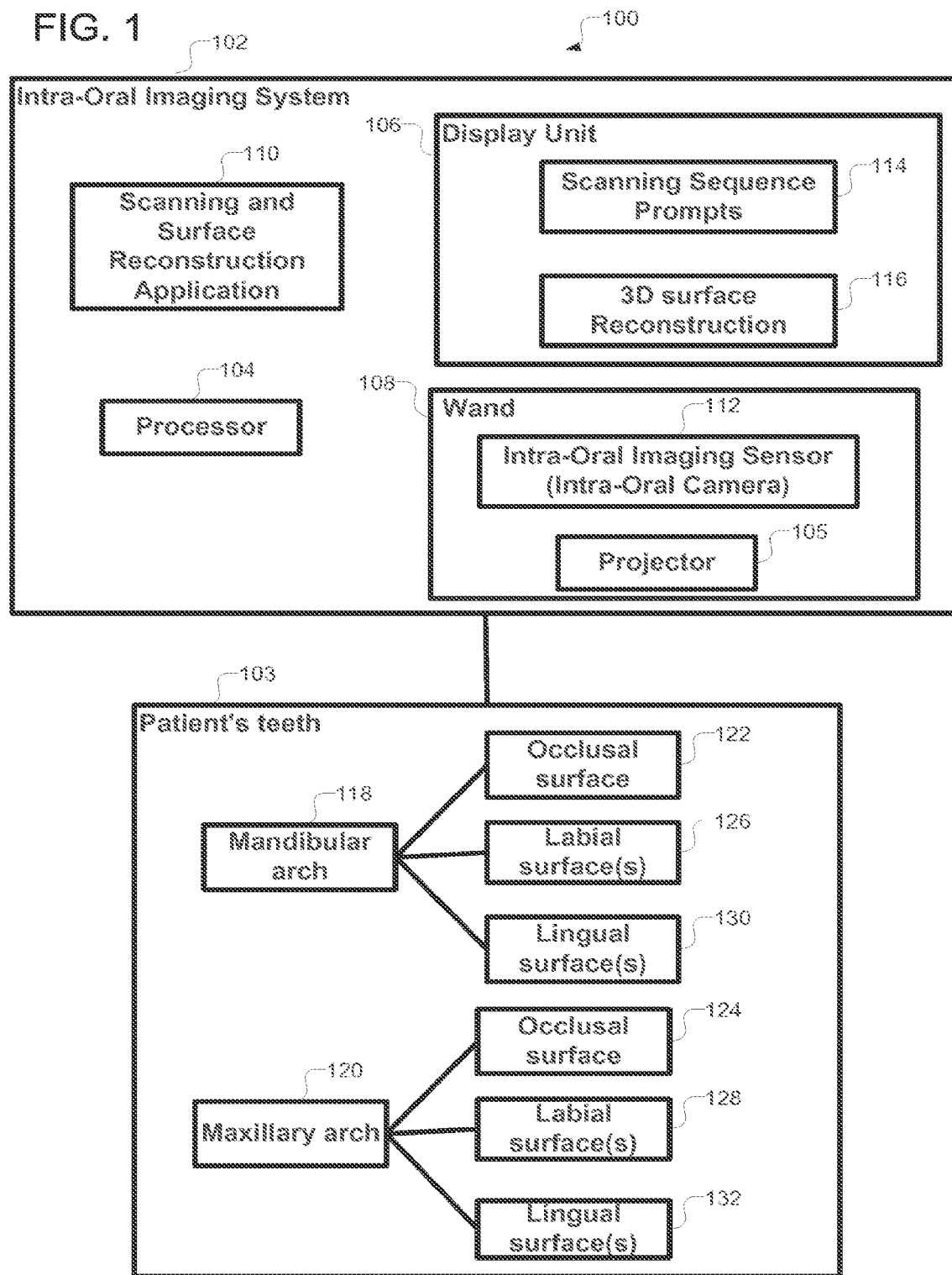
FIG. 1 illustrates a block diagram of a computing and imaging environment that includes an intra-oral imaging system used to capture images of a patient's teeth, in accordance with certain embodiments.

FIG. 1 illustrates a block diagram of a computing and imaging environment 100 that includes an intra-oral imaging system 102 used to capture images of a patient's teeth 103, in accordance with certain embodiments.

The intra-oral imaging system 102 is comprised of a processor 104, a display unit 106, a wand 108, and a scanning and surface reconstruction application 110. In certain embodiments, the intra-oral imaging system 102 may be coupled via a wired or wireless connection over a network to one or more computational devices (not shown), where the computational devices may include any suitable computational device such as a personal computer, a server computer, a mini computer, a mainframe computer, a blade computer, a tablet computer, a touch screen computing device, a telephony device, a cell phone, a mobile computational device, etc., and some of the computational devices may provide web services or cloud computing services.

A dental practitioner may hold the wand 108 inside a patient's oral cavity. An optical source (e.g. the projector 105) included in the wand 108 or coupled to the wand 108, may illuminate the oral cavity and the intra-oral imaging sensor 112 may be used to capture a plurality of digital images of structures in the oral cavity, such as the patient's teeth, gingivae, and/or, palate, and other structures, such as fillings, braces, etc. In certain embodiments the intra-oral imaging sensor 112 may comprise an intra-oral camera.

The operation of the wand 108 may be controlled by the scanning and surface reconstruction application 110 that may be implemented in software, hardware, firmware or any combination thereof. In certain embodiments, the display unit 106 of the intra-oral imaging system 104 may include a touch screen display unit that displays scanning sequence prompts 114 and three-dimensional surface reconstructions 116 of the patient's dental arches. The scanning and surface reconstruction application 110 may process the images acquired by the intra-oral imaging sensor 112 and also display the images on the display unit 106 and further transmit the images to one or more computational devices coupled via a network to the intra-oral imaging system 102.

The patient's teeth 103 that are imaged via the intra-oral imaging system 102 may include a mandibular arch 118 and a maxillary arch 120. Each of the mandibular arch 118 and the maxillary arch 120 may include an occlusal surface 122, 124, a labial surface 126, 128 and a lingual surface 130, 132.

Therefore, FIG. 1 illustrates certain embodiments in which an intra-oral imaging system 102 is used to acquire intra-oral images of the occlusal, labial, and lingual surfaces of the maxillary and mandibular arch of a patient. In the process of acquisition of images, the occlusal surface of a dental arch is acquired first via a single uninterrupted motion of the wand 108, followed by the labial and the lingual surfaces that are acquired in multiple segments. An occlusal backbone is generated from the image frames of the occlusal scan, and then the segments of the labial and lingual scans are linked to the occlusal backbone to generate the three-dimensional surface of the dental arch for real-time display on the display unit 106.

Figure 2:
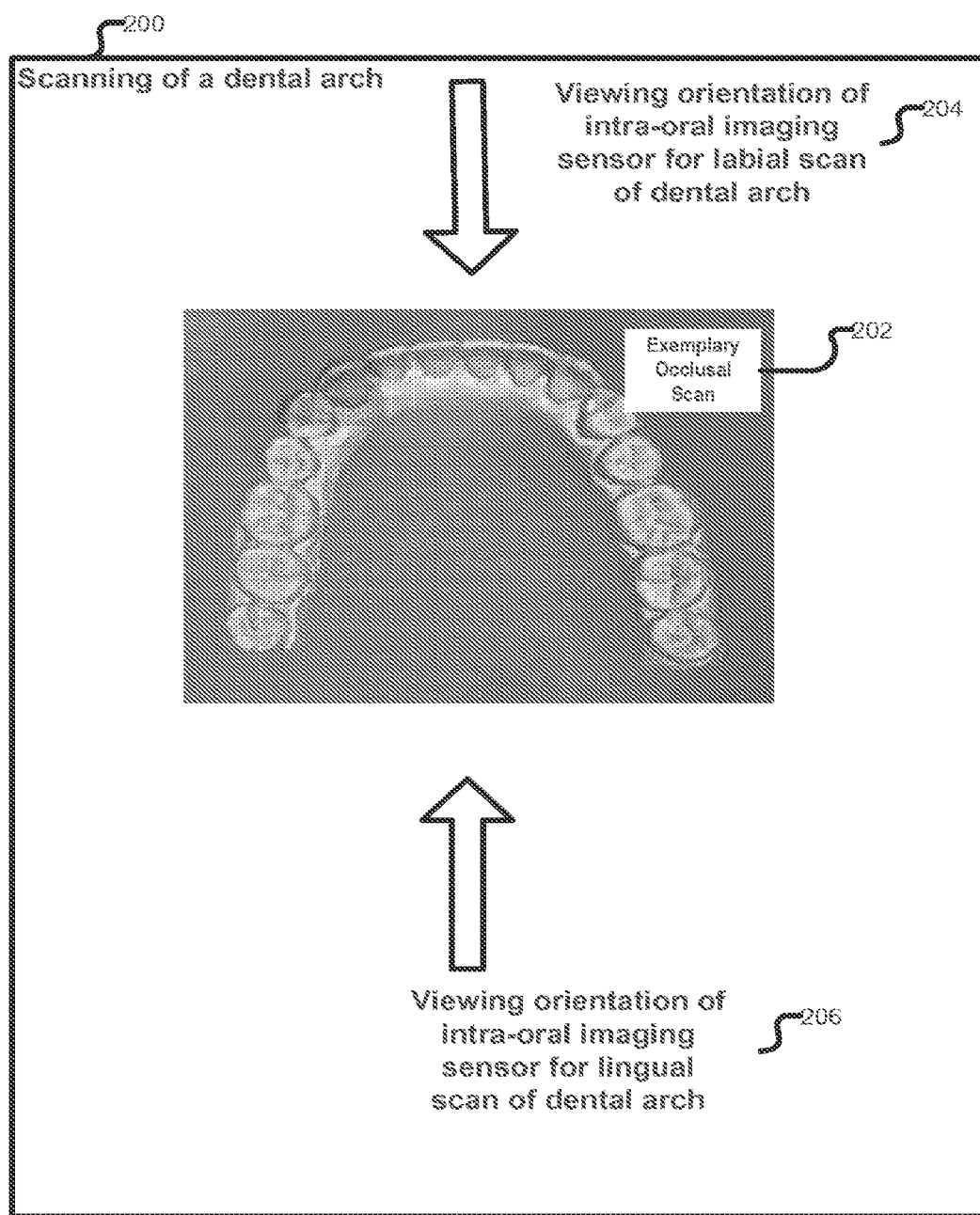
FIG. 2 illustrates a diagram that shows scanning of a dental arch, in accordance with certain embodiments.

FIG. 2 illustrates a diagram 200 that shows scanning of a dental arch, in accordance with certain embodiments. An exemplary occlusal scan 202 that is generated by gliding the wand 108 over the occlusal surface of a dental arch 118, 120 of the patient is shown. The viewing orientation of the intra-oral imaging sensor 112 for labial scan (shown via reference numeral 204) and the viewing orientation of intra-oral imaging sensor 112 for lingual scan (shown via reference numeral 206) are also shown. In the lingual scan, the side surfaces of the teeth that are predominantly faced towards the tongue are imaged. In the labial scan the side surfaces of the teeth that are predominantly faced towards the lips and cheek are imaged.

Figure 3:
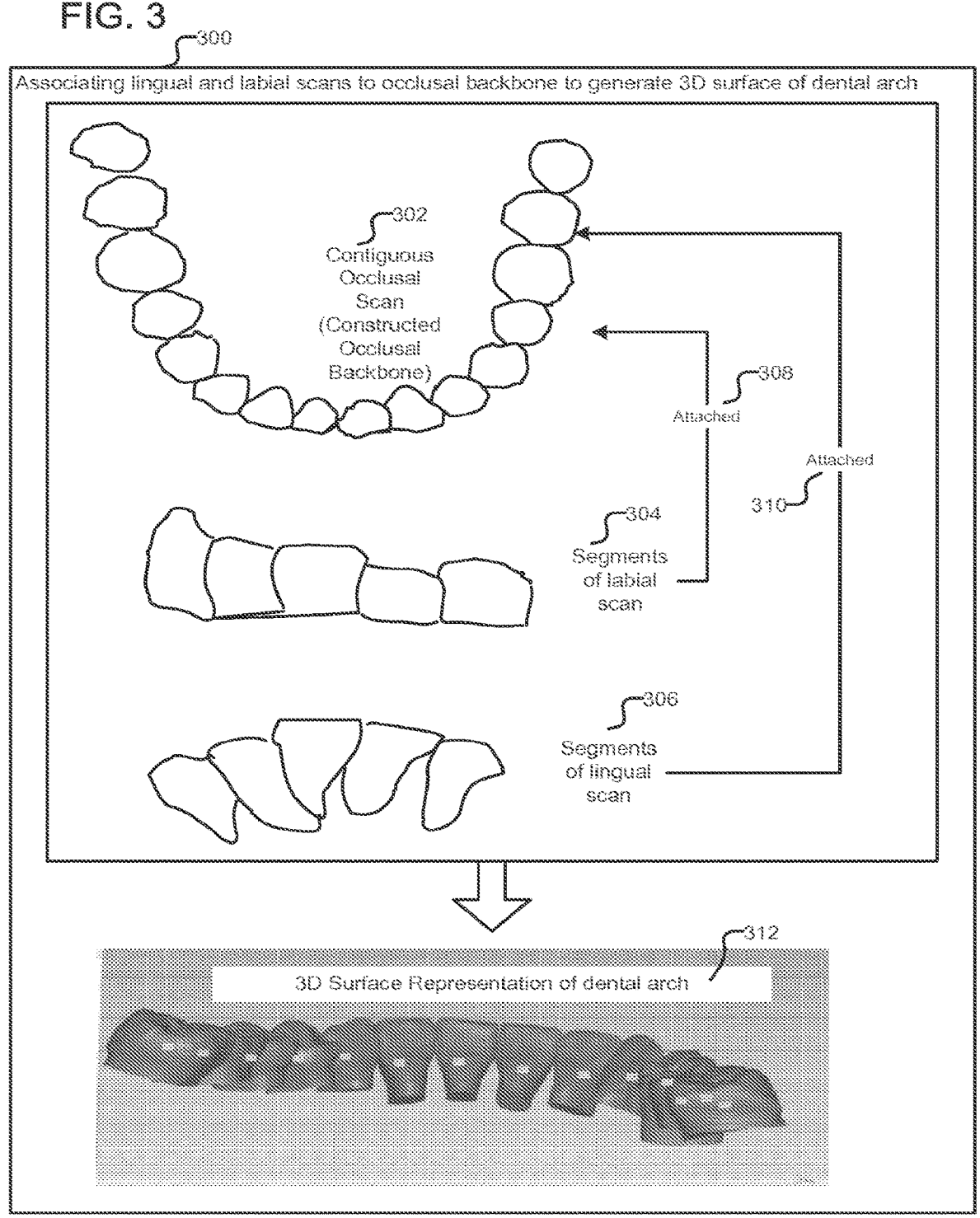
FIG. 3 illustrates a diagram that shows how lingual and labial scans are associated with an occlusal backbone to generate a three-dimensional surface representation of a dental arch, in accordance with certain embodiments.

FIG. 3 illustrates a diagram 300 that shows how lingual and labial scans are associated with an occlusal backbone to generate a three-dimensional surface representation of a dental arch, in accordance with certain embodiments.

A representation of an occlusal backbone that is constructed from a contiguous occlusal scan is shown via reference numeral 302. An exemplary segment of a labial scan 304 and an exemplary segment of a lingual scan 306 are also shown. It may be noted that multiple segments of labial scan and lingual scan may be needed to cover the entire dental arch.

In certain embodiments, the segments of the labial scan 304 and the segments of the lingual scan 306 are attached (reference numerals 308, 310) to the occlusal backbone 302 to generate a three-dimensional surface representation of the dental arch 312.

Therefore, FIG. 3 illustrates certain embodiments in which segments of labial and lingual scans are attached to an occlusal backbone to generate a three-dimensional surface representation of the dental arch for display on the display unit 106 of the infra-oral imaging system 102.

Figure 4:
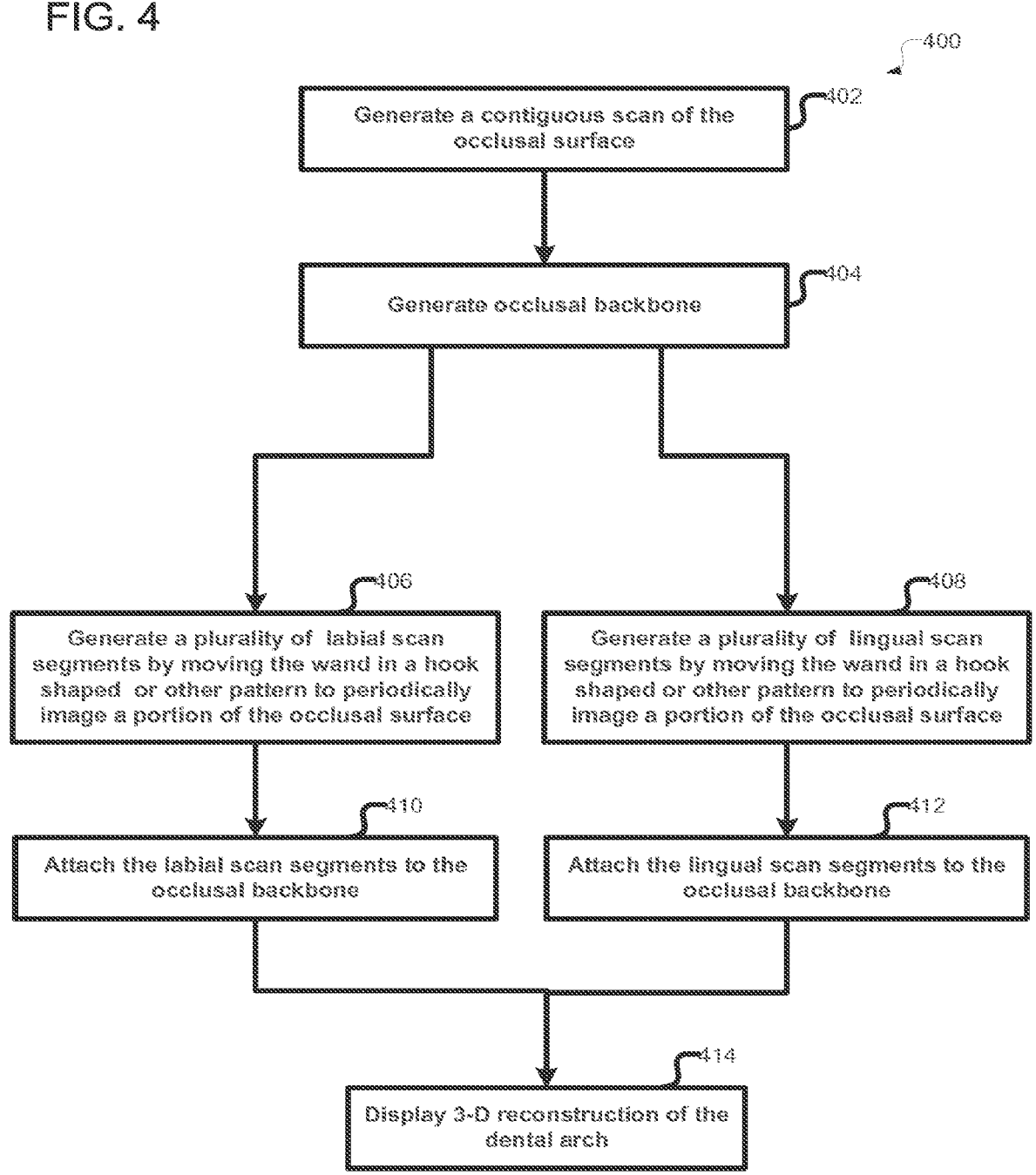
FIG. 4 illustrates a flowchart that shows how labial and lingual scans are attached to an occlusal backbone to display a three-dimensional reconstruction of the dental arch, in accordance with certain embodiments.

FIG. 4 illustrates a flowchart 400 that shows how labial and lingual scans are attached to an occlusal backbone to display a three-dimensional reconstruction of the dental arch, in accordance with certain embodiments. The operations shown in FIG. 4 may be performed via the scanning and surface reconstruction application 110 that executes operations on the processor 104 of the intra-oral imaging system 102. In certain alternative embodiments, the operations shown in FIG. 4 may be performed in one or more computational devices that are external to the intra-oral imaging system 102.

Control starts at block 402 in which the scanning and surface reconstruction application 110 generates a contiguous scan of the occlusal surface of a dental arch of the patient. A contiguous scan is a scan that scans a part or the entirety of the dental arch in a single uninterrupted motion of the wand. For example, in certain embodiments a dental practitioner may place the wand on the occlusal surface of a patient's tooth on the last molar (i.e., third molar) at one end of the dental arch and glide the wand over the occlusal surface to the last molar (i.e., third molar) on the other end of the dental arch in about 30 seconds and the corresponding scanning may be an example of a contiguous scan. It should be noted that the contiguous scan need not scan the entirety of the dental arch, but may scan a part of the dental arch. Hundreds or thousands of image frames may be acquired during the scanning process, where each image frame may be an image of a part of a tooth, an image of one tooth, or an image of a few teeth of the dental arch. Successive frames may have overlapping regions of the occlusal surface.

Control proceeds to block 404, where the hundreds or thousands of image frames are used to generate an occlusal backbone which is a three dimensional surface representation of the occlusal surface.

From block 404, control may proceed either to block 406 or block 408, where either block 406 may be performed before block 408, or block 408 may be performed before block 406.

At block 406, a plurality of labial scan segments are generated by moving the wand 108 in a hook shaped pattern (or some other exemplary pattern) to periodically image a portion of the occlusal surface while imaging the labial surface. For example, the wand 108 is moved to image the occlusal surface of a first tooth (e.g., the last, i.e., third molar at the end of a dental arch), and moved down the side surface of the first tooth towards the labial side and then along the side surface of the first tooth, second tooth, and third tooth to image a portion of the labial surface. Then the wand 108 is moved up the side surface of the third tooth and part of the occlusal surface of the third tooth is imaged to complete the scanning of a first segment of a labial surface. After that the wand 108 is gripped differently and after scanning part of the occlusal surface of the third tooth the wand 108 is moved down to the side surface of the third tooth, and the wand 108 continues to image the side surface of the third tooth, a fourth tooth, a fifth tooth along the labial surface before being moved up to scan the occlusal surface of the fifth tooth to complete the scanning of a second segment of the labial surface. Therefore, via a hook shaped or other movement pattern, at least a segment (e.g., spanning 2-6 teeth or more) of a labial scan is obtained. In alternative embodiments, other exemplary patterns besides a hook shaped pattern may be used for the movement of the wand 108. Since the wand 108 may have to be regripped (i.e., gripped in different ways) while capturing images of the labial and lingual surfaces, the scanned images of the lingual and labial surfaces may be captured in multiple segments. Each segment corresponds to images captured in a single uninterrupted movement of the wand. From block 406, control proceeds to block 410 where the labial scan segments are attached to the occlusal backbone.

At block 408, a plurality of lingual scan segments are generated by moving the wand 108 in a hook shaped pattern (or other exemplary pattern) to periodically image a portion of the occlusal surface. The plurality of lingual scan segments are attached to the occlusal backbone (at block 412).

After the labial scan segments and the lingual scan segments have all been attached to the occlusal backbone (at blocks 410, 412) then control proceeds to block 414 where the three-dimensional reconstruction of the dental arch is displayed on the display unit 106.

Therefore FIG. 4 illustrates a flowchart that shows how labial and lingual segments are attached to an occlusal backbone to display a three-dimensional surface reconstruction of a dental arch.

Figure 5:
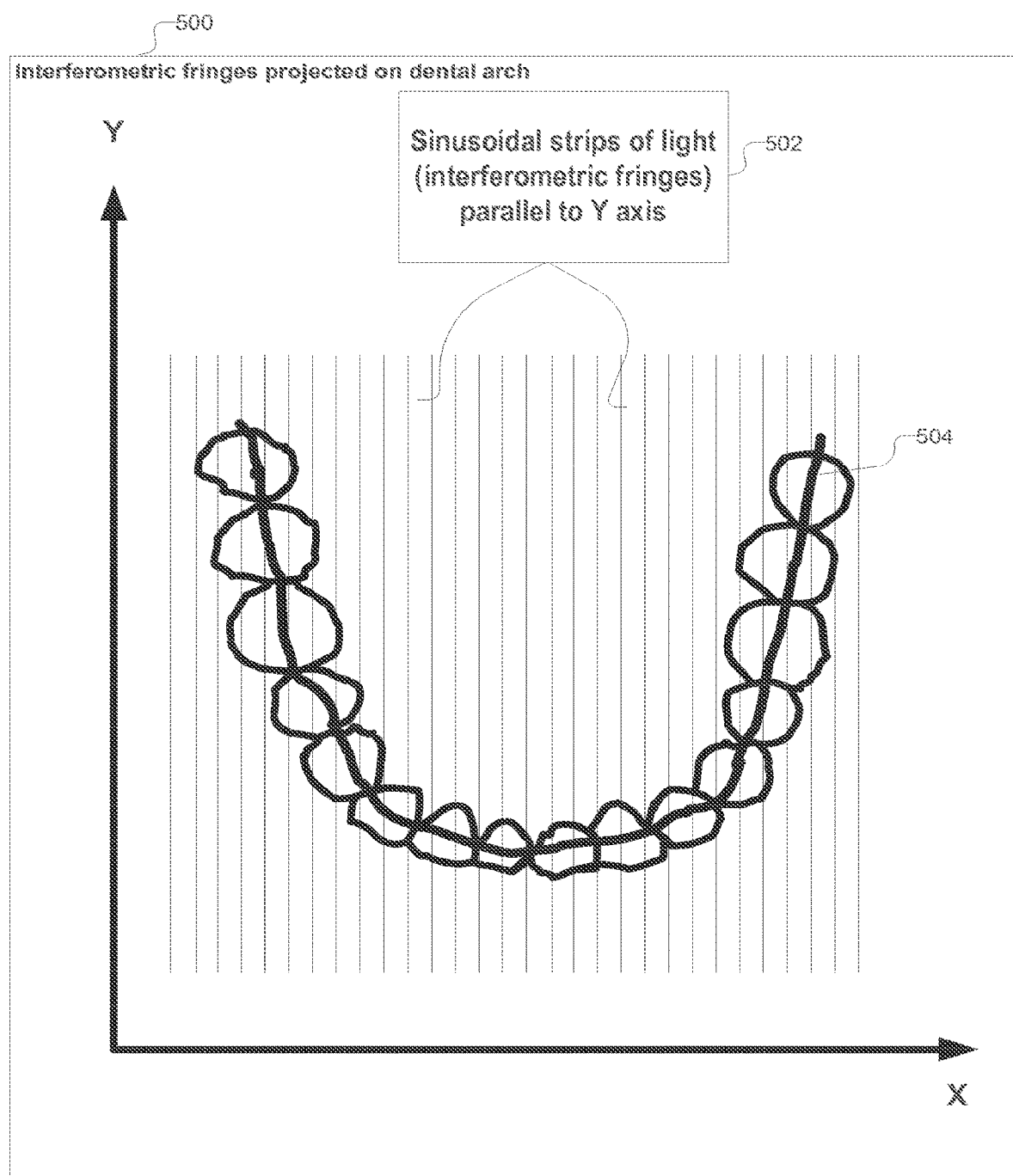
FIG. 5 illustrates a diagram that shows interferometric fringes projected on a dental arch, in accordance with certain embodiments.

FIG. 5 illustrates a diagram 500 that shows interferometric fringes 502 projected by a projector 105 on a dental arch, in accordance with certain embodiments. In certain embodiments, the intra-oral imaging system 102 is a precision opto-mechanical device, based on accordion fringe interferometer (AFI) techniques that measure three dimensional points on an object surface. The AFI technology projects (via the projector 105) two coherent beams of light, which create a precision interference fringe pattern visible on an object surface. In a simple single channel AFI system, a series of three two dimensional fringe images are acquired by an off-axis camera, with the fringe pattern at 0°, +120°, and −120°. For each camera pixel, the relative intensities of the three measurements may be mathematically combined to calculate a unique distance to the object surface, with the measurement limited by the width of one fringe. A multichannel AFI system is not limited to a measurement width of one fringe, and is, therefore, capable of rapidly measuring the topology of intra-oral features.

In FIG. 5, the wand is moved along the line 504 shown superimposed on the dental arch on which the interferometric fringes are projected. It may be observed that the movement of the wand is predominantly along the direction in which the interferometric fringes are projected. As a result, the error in surface reconstruction of the occlusal surface is reduced, in comparison to situations where interferometric fringes are not aligned with the predominant direction of the translational motion of the wand 108.

Therefore, FIG. 5 illustrates certain embodiments in which interferometric fringes are projected on the occlusal surface primarily along a direction in which the contiguous scan of the occlusal surface is performed, to reduce the amount of error in generating three-dimensional occlusal surfaces. FIG. 5 illustrates certain embodiments of an imaging system 102, comprising a projector 105 that projects interferometric fringes on an occlusal surface of at least a part of one arch of a dentition primarily along an anteriorposterior direction, and an imaging sensor 112 that is used to view the interferometric fringes. In certain embodiments, the imaging system 102 is configured to generate a contiguous scan of an occlusal surface, and associate at least one additional surface to the contiguous scan of the occlusal surface. In certain embodiments, the at least one additional surface comprises a plurality of labial surfaces and a plurality of lingual surfaces.

Figure 6:
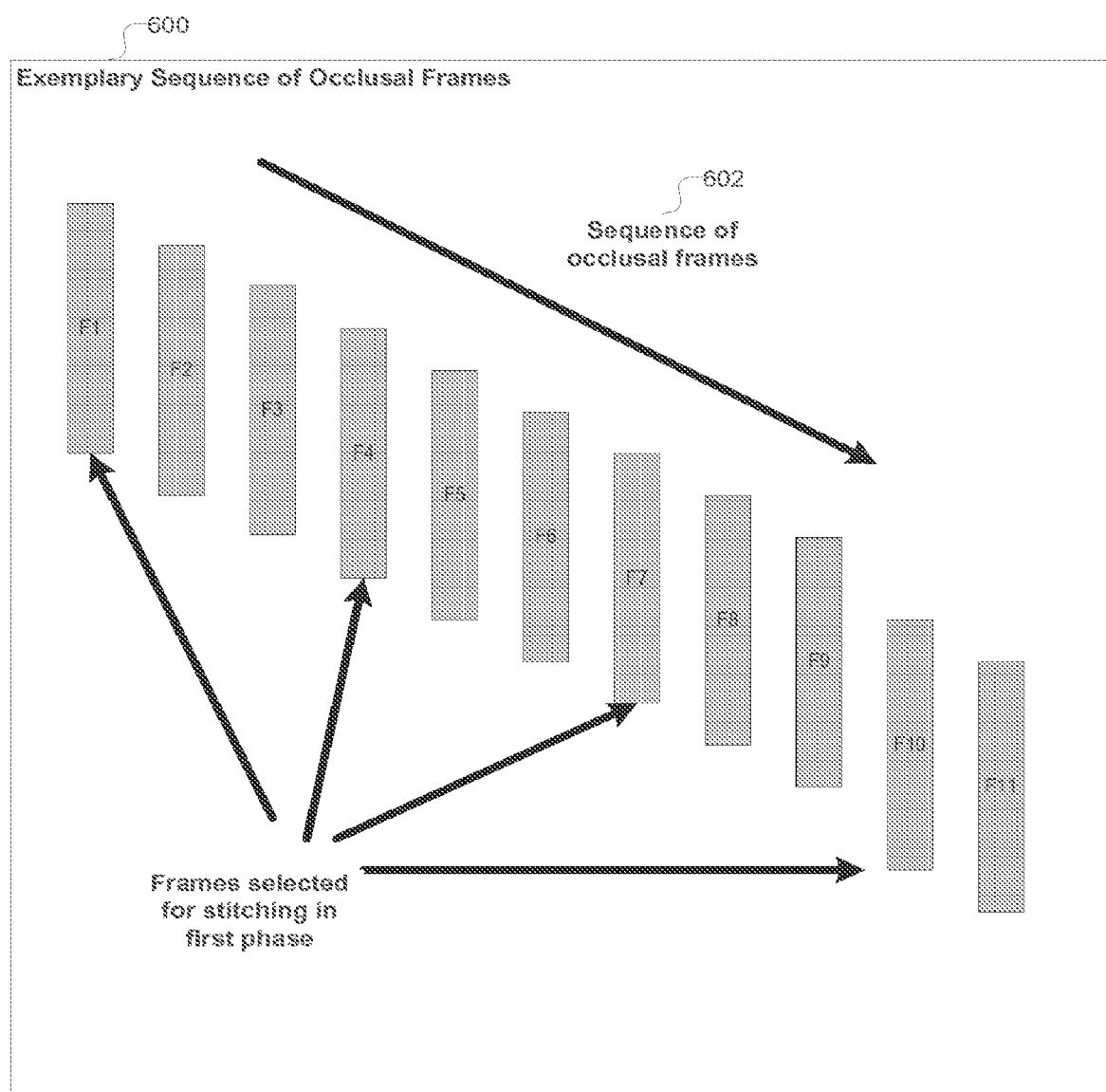
FIG. 6 illustrates an exemplary sequence of occlusal frames, in accordance with certain embodiments.

FIG. 6 illustrates an exemplary sequence 600 of occlusal frames, in accordance with certain embodiments. The occlusal frames F1, F2, F3, F4, F5, F6, F7, F8, F9, F10, F11 (shown via reference numeral 602) are acquired successively while traversing the occlusal surface of the dental arch, and each occlusal frame encompasses part of a tooth, a single tooth, or a plurality of teeth. There is overlap of the occlusal surface between two successive frames. For example, both frame F1 and frame F2 may image a section of the same tooth.

In certain embodiments, to minimize the effects of noise and certain other image characteristics, frames which overlap by about 50% are selected to construct the occlusal backbone. In other embodiments, frames with a different percentage of overlap may be selected to construct the occlusal backbone. In situations where the noise is random, an overlap of about 50% between two flumes may provide adequate translational movement and not too much rotational movement to tit the two frames to each other via a process of statistical noise elimination. In other embodiments frames may be selected based on an overlap that may vary between 15% to 85%. In other embodiments, the optimal percentage of overlap may be determined based on analysis of data included or associated with the frames. In certain embodiments, the optimal percentage for the overlap may depend of the noise characteristics.

For example, FIG. 6 shows that frames F1, F4, F7, and F10 are selected to be stitched together (i.e., to be fitted during surface reconstruction) in a first phase of the construction of the occlusal backbone. Frames F4 and F1 have an overlapping region of about 50%, frames F7 and F4 have an overlapping region of about 50%, and frames F7 and F10 have an overlapping region of about 50%.

Figure 7:
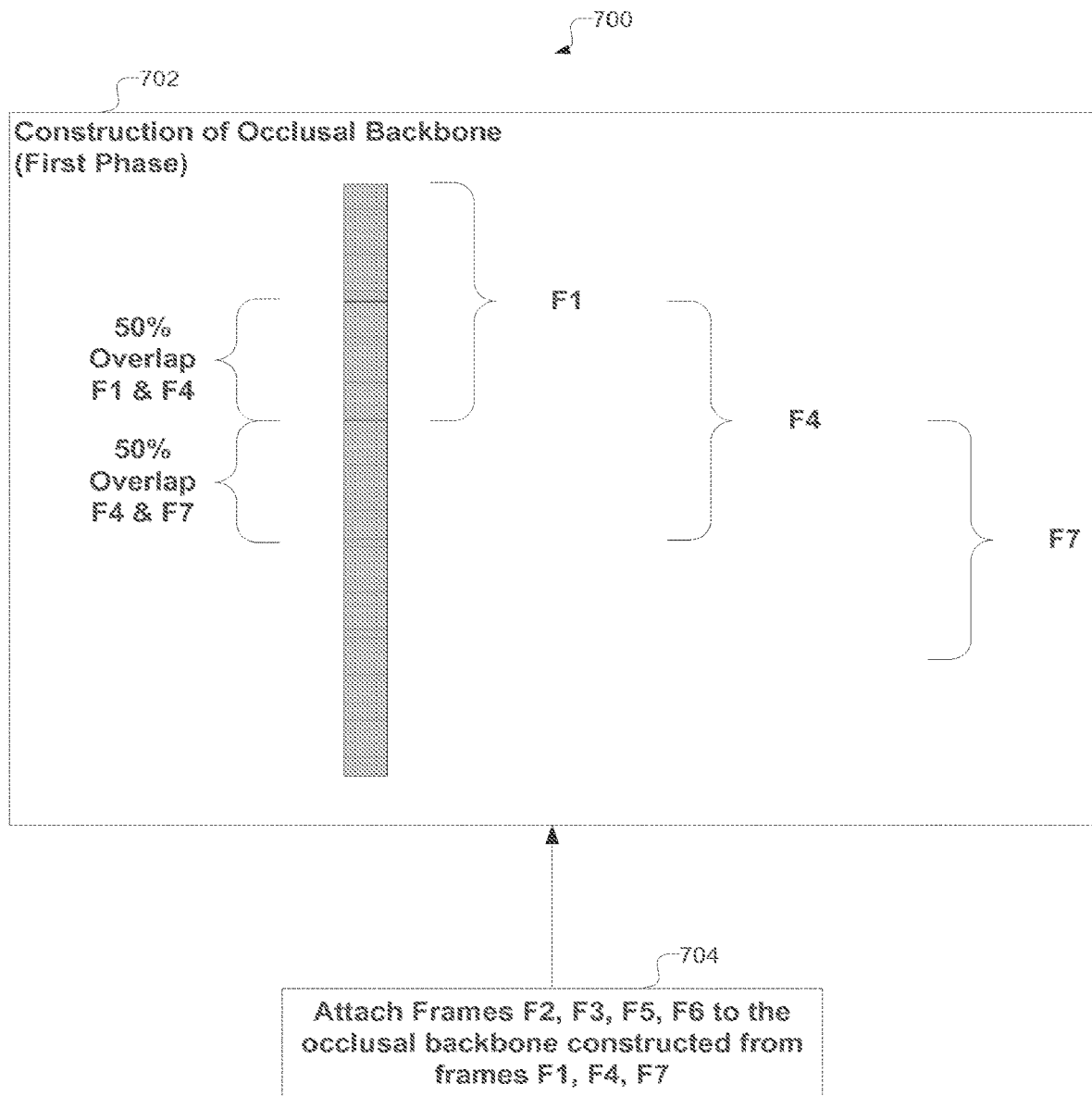
FIG. 7 illustrates a diagram that shows how selected frames with an exemplary 50% overlap are used to construct the occlusal backbone, in accordance with certain embodiments.

FIG. 7 illustrates a diagram 700 that shows how selected frames with around 50% overlap are used to construct the occlusal backbone, in accordance with certain embodiments.

In FIG. 7 that is based on the frames F1 . . . F11 shown via, reference numeral 602 in FIG. 6, Frames F4 and F1 have an overlapping region of about 50%, frames F7 and F4 have an overlapping region of about 50%, and these frames F1, F4, F7 are stitched together in a first phase (shown via reference numeral 702) to generate a rough occlusal backbone. Then in a second phase frames F2, F3, F5, F6 are attached (shown via, reference numeral 704) to the rough occlusal backbone to generate a more accurate occlusal backbone.

Figure 8:
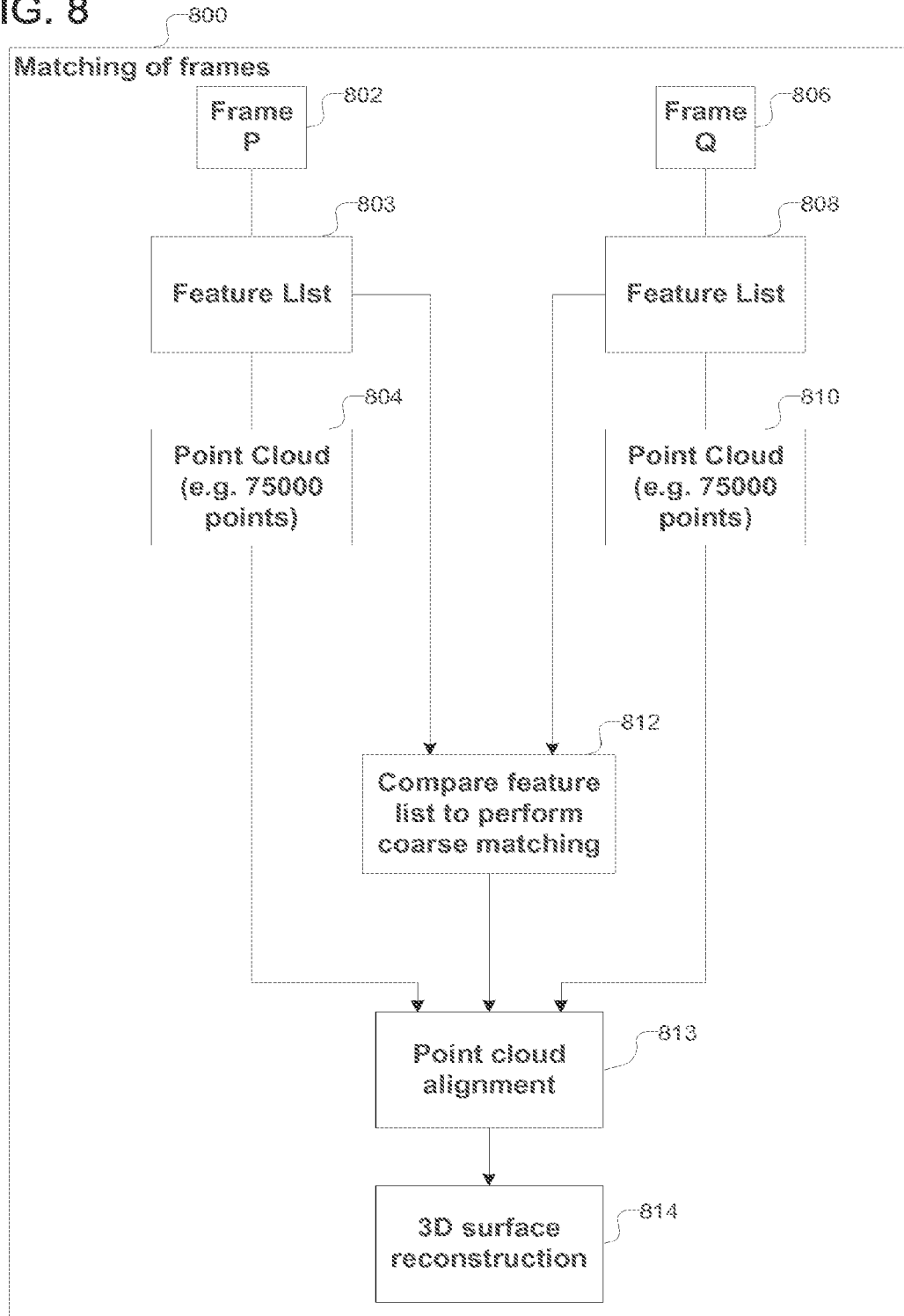
FIG. 8 illustrates a diagram that shows how frames are matched to construct the occlusal backbone, in accordance with certain embodiments.

FIG. 8 illustrates a diagram 800 that shows how frames are matched to construct the occlusal backbone, in accordance with certain embodiments. Frame P 802 has an associated feature list 803 and a point cloud 804 of about 7500 points, and frame Q 806 has an associated feature list 808 and a point cloud 810 of about 75000 points. Matching frame P 802 to frame Q 806 in three dimensions, by using the roughly 75000 point cloud pairs is very time consuming. To display the three-dimensional surface reconstruction in real-time while scanning is being performed, the feature lists 803 and 808 are used to match frame P 802 to frame Q 806 and perform a coarse matching (block 812). The feature lists 802, 808 are relatively faster to match. Once a coarse matching is obtained, then a point cloud alignment may be performed with the point clouds 804, 810 or other mechanisms may be used to refine the match as shown via reference numeral 813, to perform (at block 814) the three-dimensional reconstruction.

Therefore, FIGS. 6, 7, and 8 illustrate certain embodiments in which an occlusal backbone is constructed by first using frames that overlap by about 50% (or on some other percentage based on noise or other characteristics), and then other frames are attached to the occlusal backbone. During construction of the optical backbone frames are first matched via matching feature lists to secure coarse fits, before using point clouds to refine the fitting of frames for three-dimensional surface reconstruction.

Figure 9:
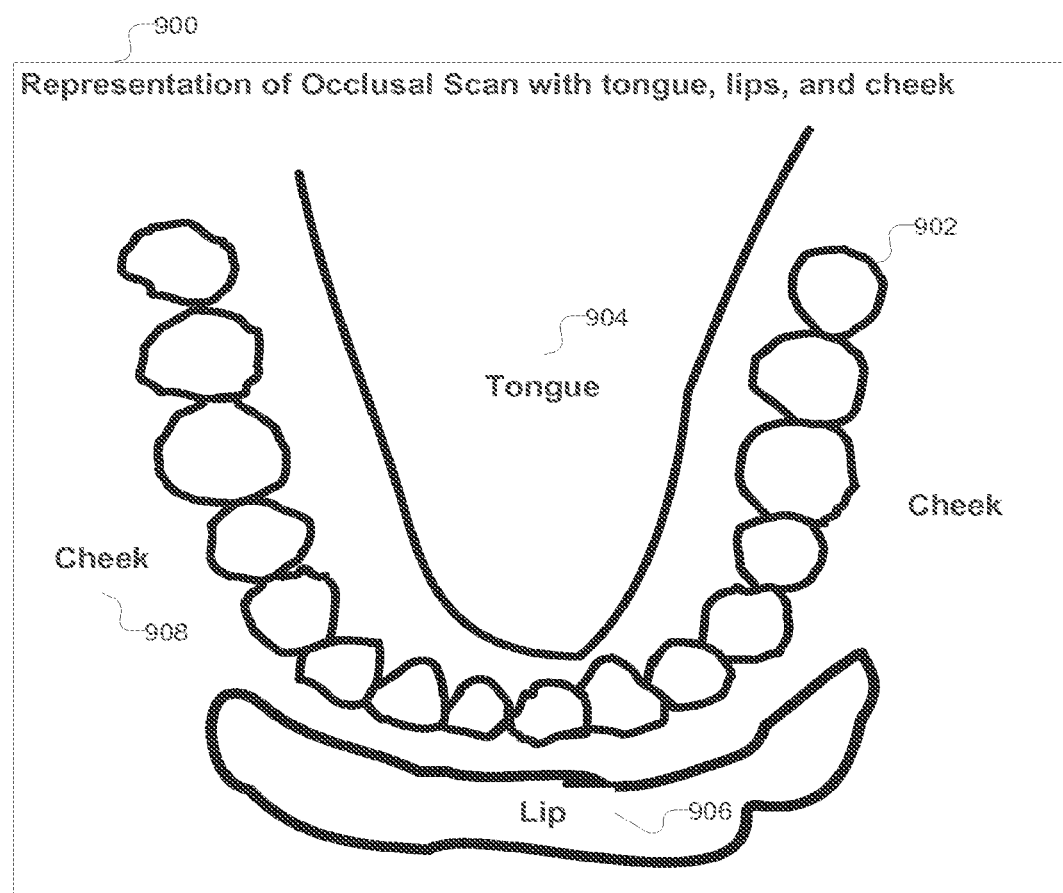
FIG. 9 illustrates a diagram that shows a representation of an occlusal scan with tongue, lips, and cheek, in accordance with certain embodiments.

FIG. 9 illustrates a diagram 900 that shows a representation of an occlusal scan 902 with tongue 904, lips 906, and cheek 908, in accordance with certain embodiments. The tongue, lips, and cheek may hide portions of the occlusal surface of the dental arch when the occlusal scan of the dental arch is being acquired. The frames of the occlusal scan shows images of the teeth overlapped with portions of the tongue, lips, and cheek, and potentially other elements. The portions that represent the tongue, cheek, and lips are removed from the occlusal backbone.

Figure 10:
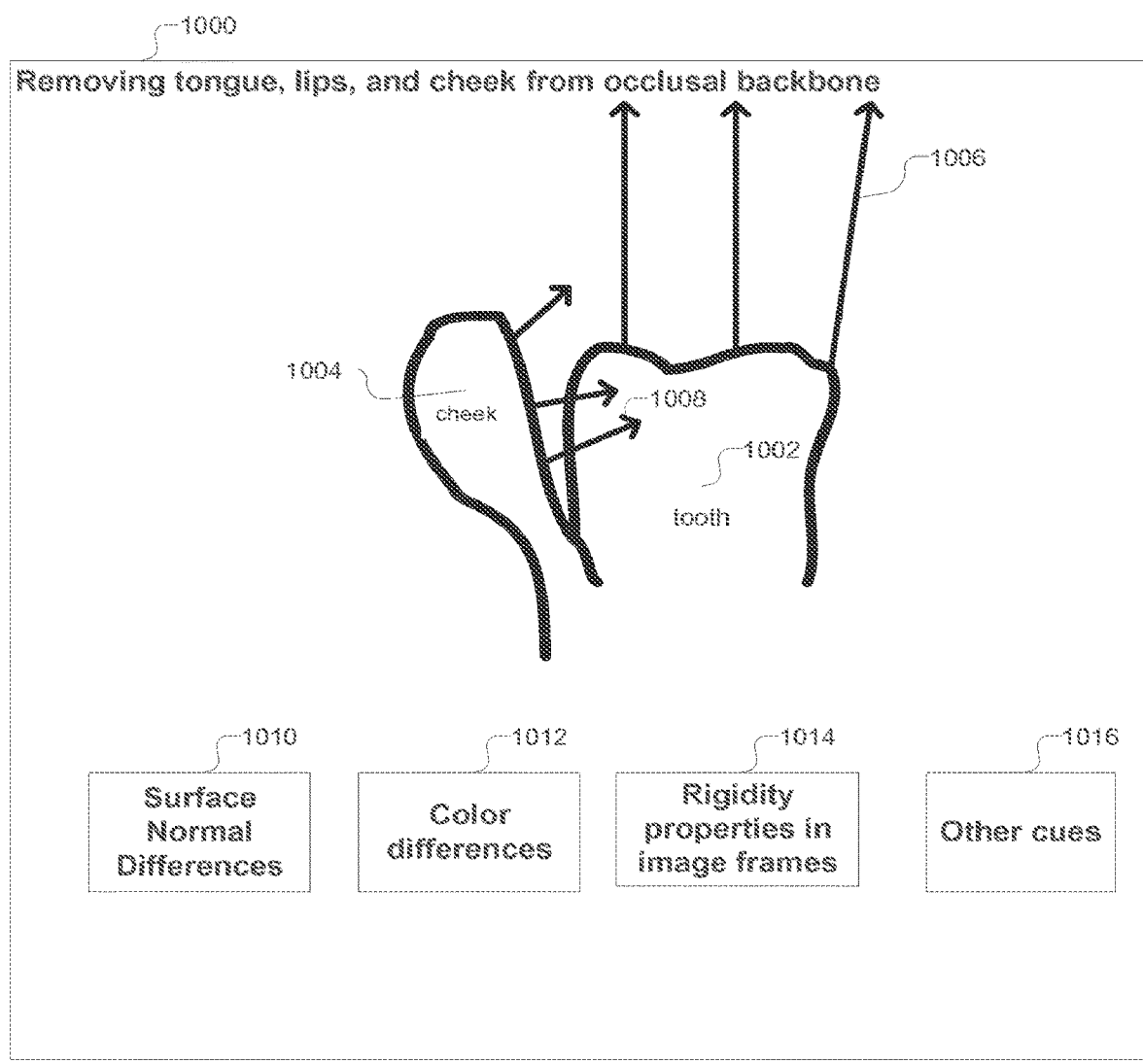
FIG. 10 illustrates a diagram that shows how tongue, lips, and cheek are removed from the occlusal backbone, in accordance with certain embodiments.

FIG. 10 illustrates a diagram 100 that shows how tongue, lips, and cheek are removed from the occlusal backbone, in accordance with certain embodiments. In FIG. 10 an exemplary tooth 1002 and cheek 1004 are shown. It can be observed that the surface normals 1006 of the tooth 1002 are oriented significantly differently than the surface normals 1008 of the cheek 1004. Additionally, if color images are taken there may be color differences between the tooth and cheek. Since cheek is non-rigid and tooth is rigid, image characteristics in a sequence of frames may be used to determine non-rigid objects like cheek (or lips or tongue). Therefore, by determining one or more of surface normal differences 1010, color differences 1012, rigidity property differences 1014, and other cues 1016 the areas of the occlusal scan that represent cheek, tongue, and lips are removed from the occlusal backbone.

Figure 11:
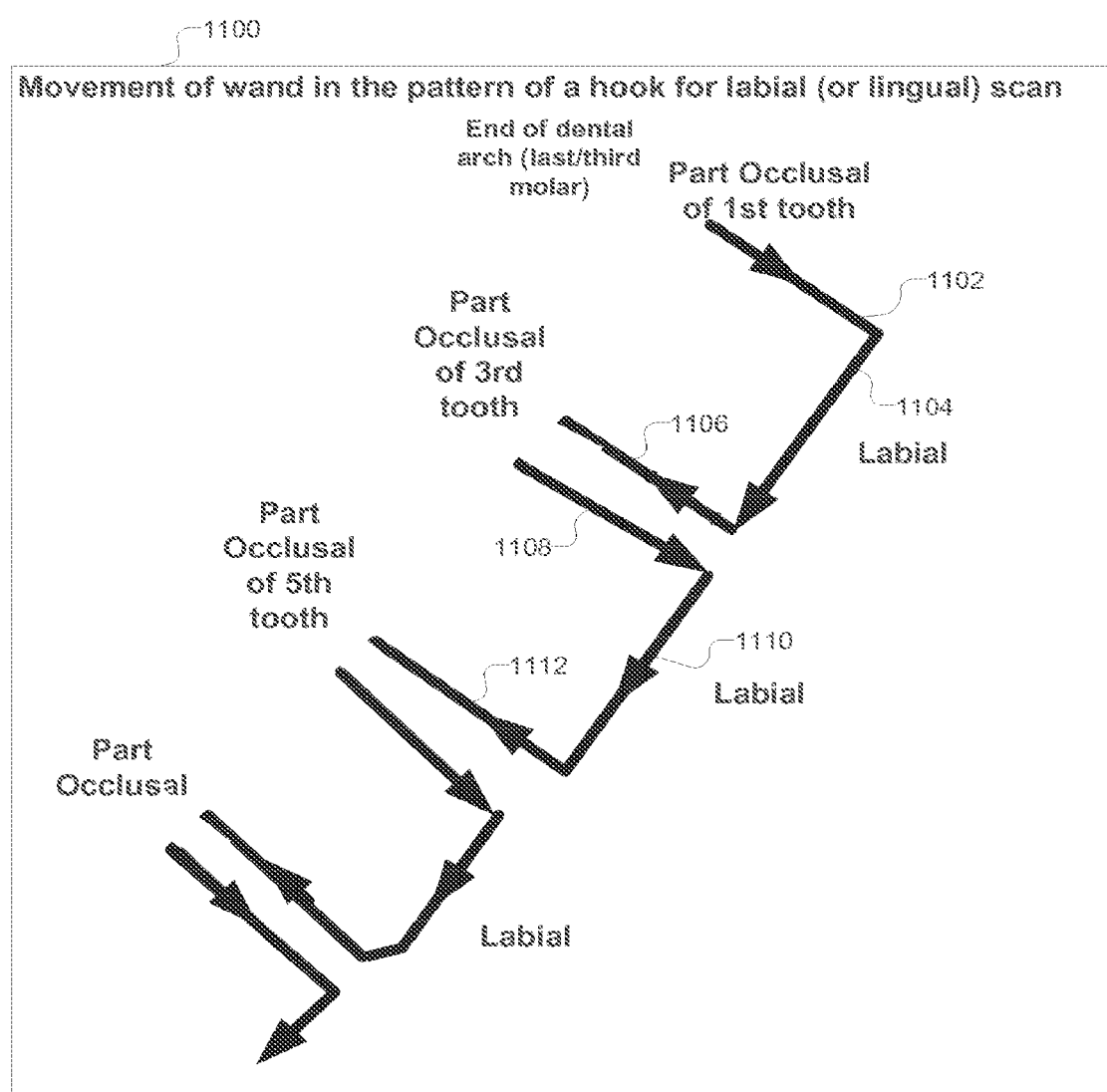
FIG. 11 illustrates a diagram that shows the movement of a wand in an exemplary pattern for labial or lingual scans, in accordance with certain embodiments.

FIG. 11 illustrates a diagram 1100 that shows the movement of a wand 108 in an exemplary pattern, such as in a hook shaped pattern, for labial or lingual scans, in accordance with certain embodiments. Other predetermined movement patterns besides a hook shaped pattern may be used in alternative embodiments.

In FIG. 11, the wand may be placed on the occlusal surface of a first tooth (e.g., the third molar at the end of a dental arch), and moved down (reference numeral 1102) the side surface of the first tooth towards the labial side and then along (reference numeral 1104) the side surface of the first tooth, a second tooth, and a third tooth to image a portion of the labial surface. Then the wand is moved up (reference numeral 1106) the side surface of the third tooth and part of the occlusal surface of the third tooth is imaged. Therefore reference numerals 1102, 1104, 1106 show a first segment being acquired for a labial scan.

Subsequent to the first segment being acquired for a labial scan, the wand may have to be gripped once again, and after scanning part of the occlusal surface of the third tooth, the wand is moved down (reference numeral 1108) to the side surface of the third tooth and the wand continues to image the side surface of the third tooth, a fourth tooth, a fifth tooth along (reference numeral 1110) the labial surface before being moved up (reference numeral 1112) to scan the occlusal surface of the fifth tooth. Therefore reference numerals 1108, 1110, 1112 show a second segment being acquired for a labial scan.

Therefore, via a hook shaped movement pattern at least a segment (e.g., spanning 2-6 teeth or more) of a labial scan is obtained. Multiple segments of labial scan and multiple segments of lingual scan are generated to image the dental arch.

Therefore, FIG. 11 shows certain embodiment, in which by moving the wand 108 in a hook shaped pattern or in accordance with other predetermined patterns, a plurality of segments of the labial and lingual surfaces are obtained, where each segment also includes portions of the occlusal surface that may be used to map the lingual and labial segments to the occlusal backbone. In certain embodiments, both the labial and lingual surfaces have three or four segments each. In other embodiments, the labial and lingual surfaces may be captured in a different number of segments.

Figure 12:
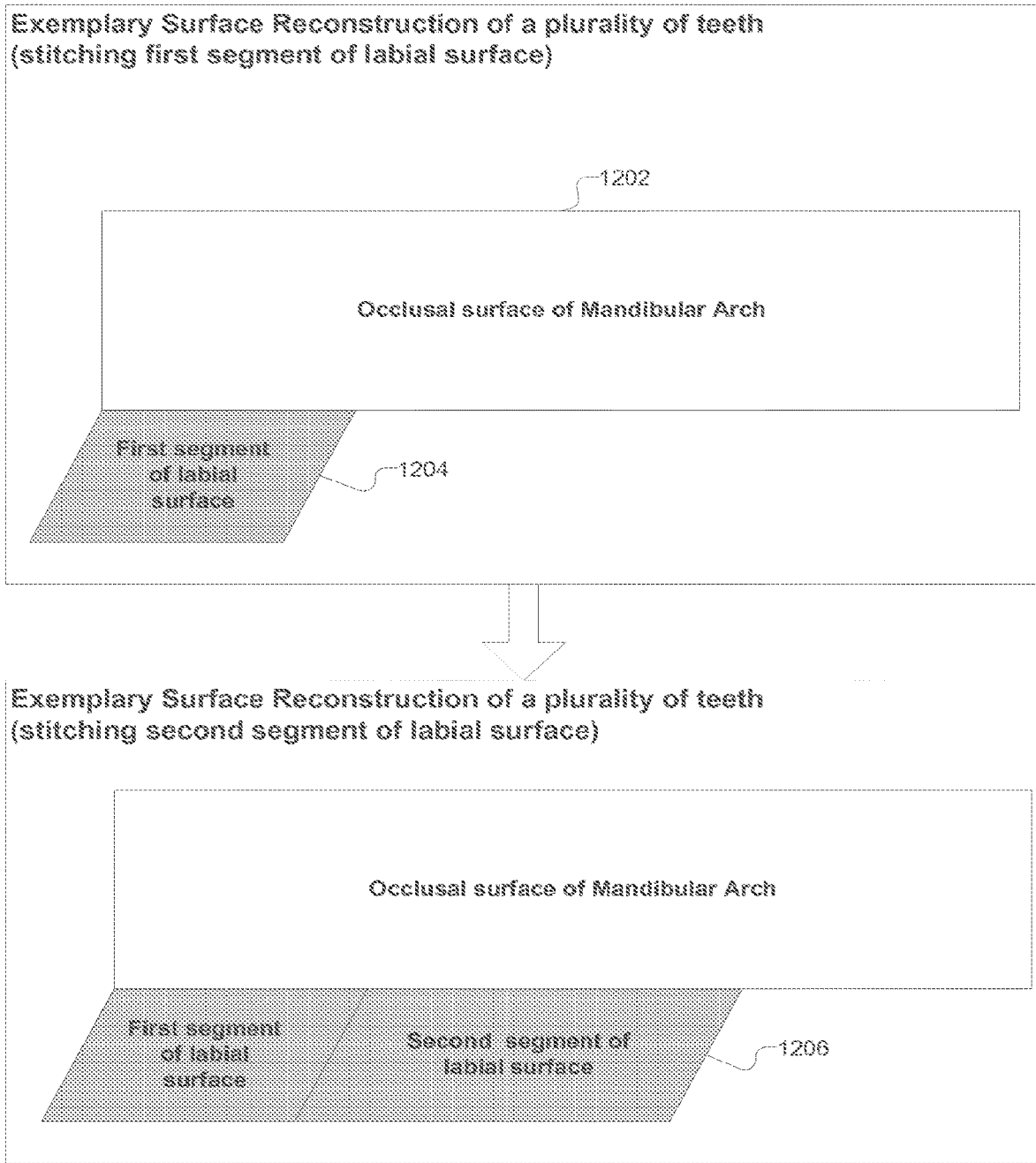
FIG. 12 illustrates a first phase of an exemplary surface reconstruction of a plurality of teeth by stitching first and second segments of a labial surface to an occlusal backbone, in accordance with certain embodiments.

FIG. 12 illustrates a first phase 1200 of an exemplary surface reconstruction of a plurality of teeth by stitching first and second segments of a labial surface to an occlusal backbone, in accordance with certain embodiments. An occlusal surface of the mandibular arch 1202 represented via the occlusal backbone is shown and the first segment 1204 of the labial surface is stitched (i.e., mapped and fitted) to the occlusal backbone. Then the second segment of the labial surface 1206 is fitted to the occlusal backbone and the first segment.

Figure 13:
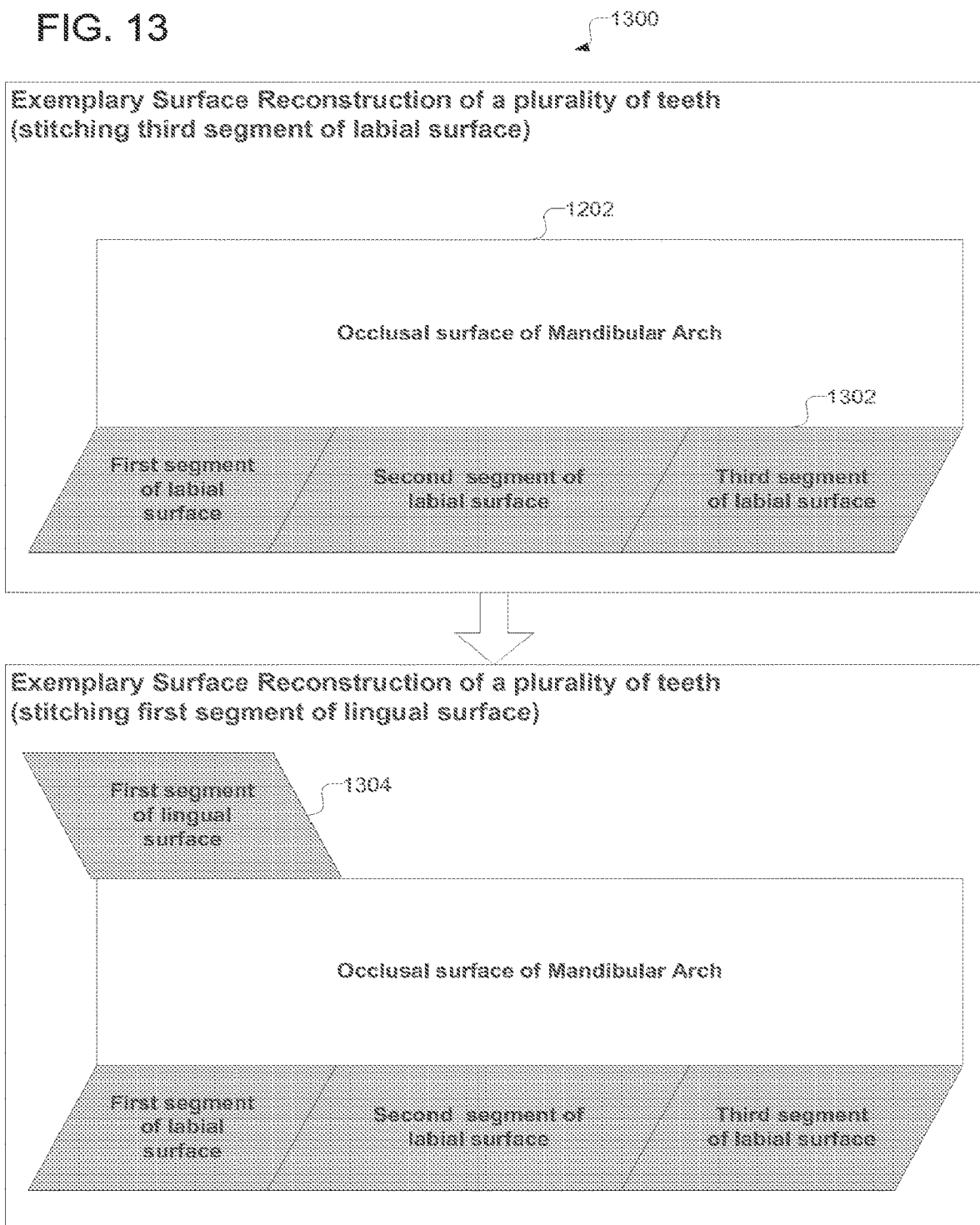
FIG. 13 illustrates a second phase of an exemplary surface reconstruction of a plurality of teeth by stitching a third segment a labial surface and a first segment of a lingual surface to an occlusal backbone, in accordance with certain embodiments.

FIG. 13 illustrates a second phase 1300 of an exemplary surface reconstruction of a plurality of teeth by stitching a third segment a labial surface and a first segment of a lingual surface to an occlusal backbone, in accordance with certain embodiments. An occlusal surface of the mandibular arch represented via the occlusal backbone 1202 is shown and the third segment of the labial surface 1302 is stitched (i.e., mapped and fitted) to the occlusal backbone and the second segment of the labial surface. Thus the labial surface is completely fitted to the occlusal surface. Then the first segment of the lingual surface 1304 is fitted to the occlusal backbone.

Figure 14:
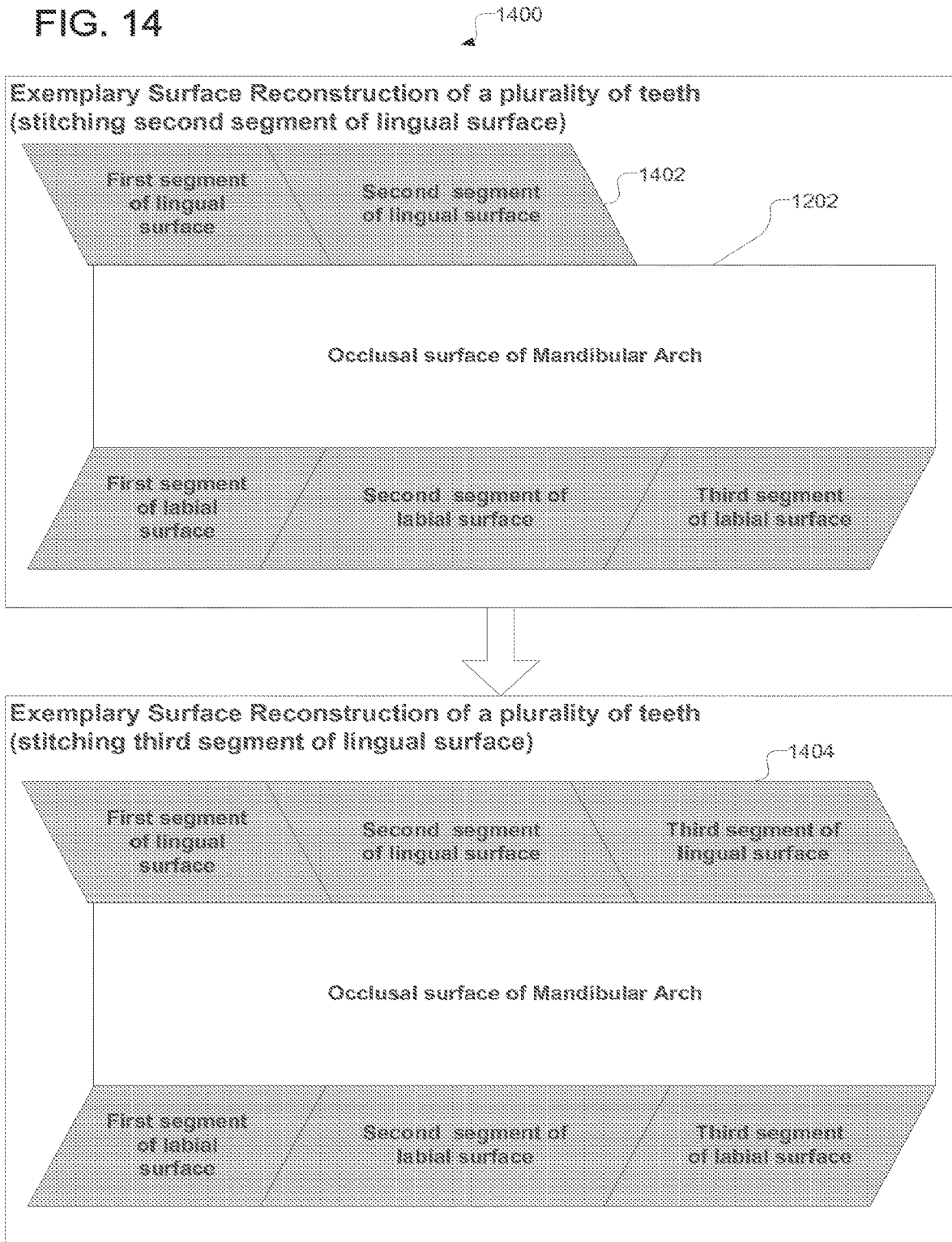
FIG. 14 illustrates a third phase of an exemplary surface reconstruction of a plurality of teeth by stitching second and a third segments of a lingual surface to an occlusal backbone, in accordance with certain embodiments.

FIG. 14 illustrates a third phase 1400 of an exemplary surface reconstruction of a plurality of teeth by stitching second and third segments of a lingual surface to an occlusal backbone, in accordance with certain embodiments. An occlusal surface of the mandibular arch represented via the occlusal backbone 1202 is shown and a second segment of the lingual surface 1402 is stitched (i.e., mapped and fitted) to the occlusal backbone and the first segment of the lingual surface. Then the third segment of the lingual surface 1404 is fitted to the occlusal backbone and the second segment of the lingual surface. As a result all segments of the lingual and labial surfaces are fitted to the occlusal backbone and the three dimensional surface reconstruction of the dental arch is completed.

Figure 15:
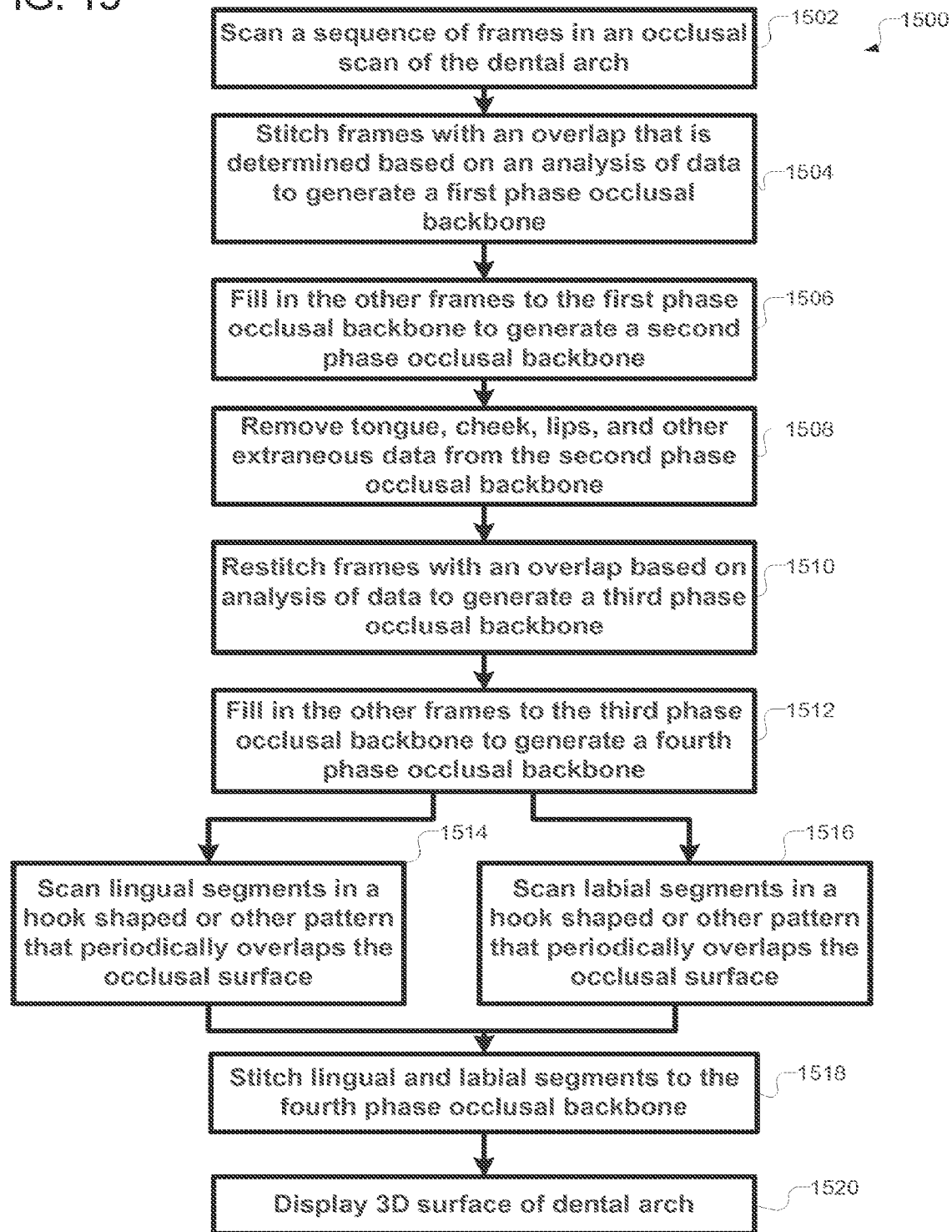
FIG. 15 illustrates a flowchart that shows how an accurate occlusal backbone is generated by selecting frames that overlap, and by removing areas that represent the tongue, cheek, and lips, and how labial and lingual scans are attached to the occlusal backbone to display a three-dimensional reconstruction of the dental arch, in accordance with certain embodiments.

FIG. 15 illustrates a flowchart 1500 that shows how an accurate occlusal backbone is generated by selecting frames that overlap by a determined amount (e.g., 50% overlap) and by removing areas that represent the tongue, cheek, and lips, and how labial and lingual scans are attached to the occlusal backbone to display a three-dimensional reconstruction of the dental arch, in accordance with certain embodiments. The operations shown in FIG. 15 may be performed via the scanning and surface reconstruction application 110 that executes operations on the processor 104 of the intraoral imaging system 102. In certain alternative embodiments, the operations shown in FIG. 15 may be performed in one or more computational devices that are external to the intra-oral imaging system 102.

Control starts at block 1502 in which the intraoral imaging system 102 scans a sequence of frames in an occlusal scan of the dental arch. Frames with an overlap (e.g., 50% overlap) that are determined based on analysis of data are stitched, i.e., fitted, (at block 1504) to generate a first phase occlusal backbone. The intra-oral imaging system 102 fills (at block 1506) the other frames (e.g., the frames that did not have around 50% overlap) to the first phase occlusal backbone to generate a second phase occlusal backbone.

The intra-oral imaging system 102 removes (at block 1508) the tongue, cheek, lips and other extraneous data from the second phase occlusal backbone. Control proceeds to block 1510 in which the frames with an overlap (e.g., 50% overlap) based on the analysis of date are stitched once again to generate a third phase occlusal backbone. This restitching is relatively fast as it can start with positions and orientations determined in the second phase occlusal backbone which are fairly accurate, and the new positions and orientations are a minor deviation from the previous positions and orientations. The other frames are filled in the third phase occlusal backbone to generate a fourth phase occlusal backbone. It should be noted that the fourth phase occlusal backbone is more accurate in position and orientation and does not have tongue, cheek, or lip data.

The wand 108 of the intra-oral imaging system is used to scan (at blocks 1514 and 1516) labial and lingual segments in a hook shaped or some other pattern that periodically overlaps the occlusal surface. From blocks 1514 and 1516 control proceeds to block 1518 in which the intra-oral imaging system 102 stitches lingual and labial segments to the fourth phase occlusal backbone and displays (at block 1520) the three-dimensional surface of dental arch on the display unit 106.

Figure 16:
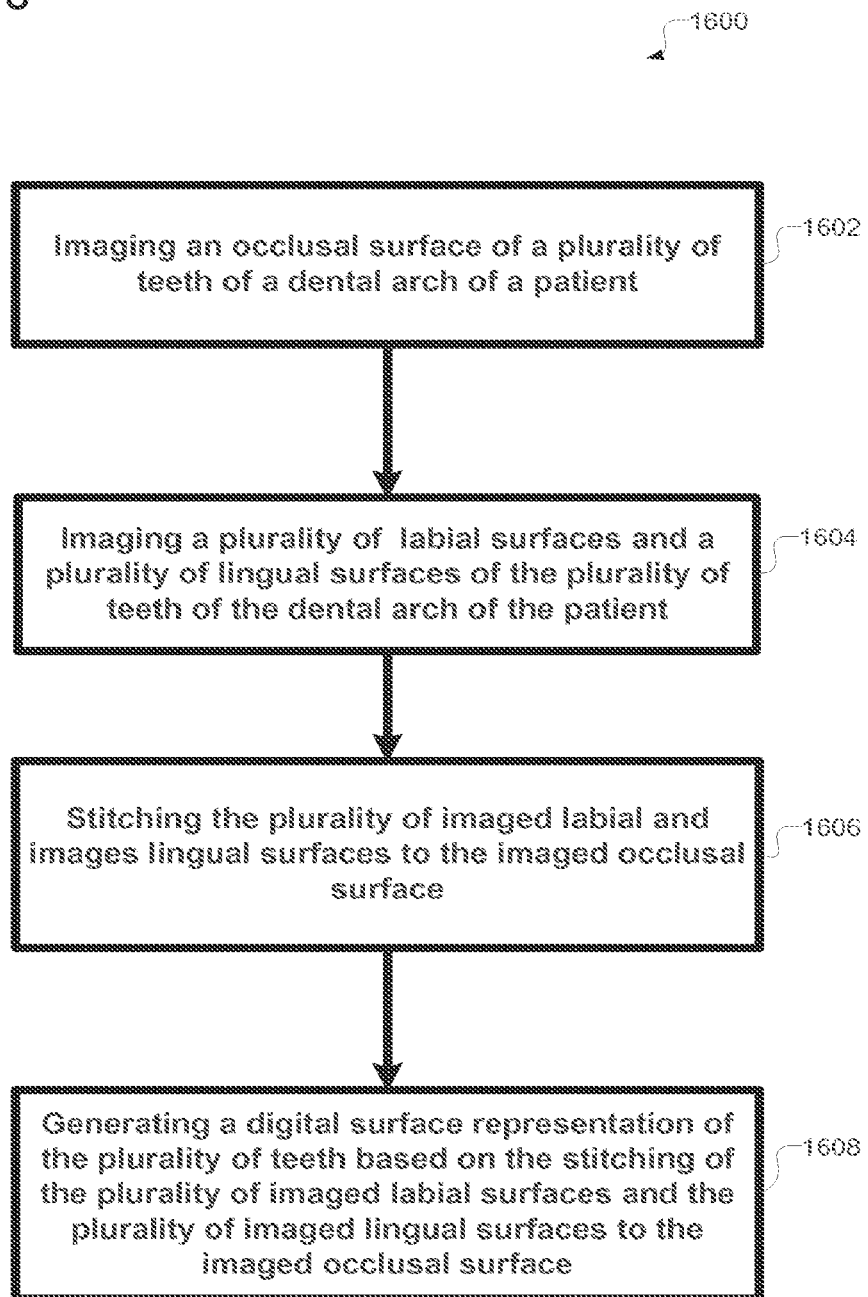
FIG. 16 illustrates a flowchart that shows how labial and lingual scans are attached to an occlusal backbone to display a three-dimensional reconstruction of the dental arch, in accordance with certain embodiments.

FIG. 16 illustrates a flowchart 1600 that shows how labial and lingual scans are attached to an occlusal backbone to display a three-dimensional reconstruction of the dental arch, in accordance with certain embodiments. The operations shown in FIG. 16 may be performed via the scanning and surface reconstruction application 110 that executes operations on the processor 104 of the intra-oral imaging system 102. In certain alternative embodiments, the operations shown in FIG. 16 may be performed in one or more computational devices that are external to the intra-oral imaging system 102.

Control starts at block 1602 in which the wand 108 is used to image an occlusal surface of a plurality of teeth of the dental arch of the patient. A plurality of labial surfaces and a plurality of lingual surfaces of the plurality of teeth of the dental arch of the patient are also imaged (at block 1604).

The scanning and surface reconstruction application 110 stitches (at block 1606) the plurality of imaged labial and images lingual surfaces to the imaged occlusal surface. A digital surface representation of the plurality of teeth based on the stitching of the plurality of imaged labial surfaces and the plurality of imaged lingual surfaces to the imaged occlusal surface is generated (at block 1608).

Figure 17:
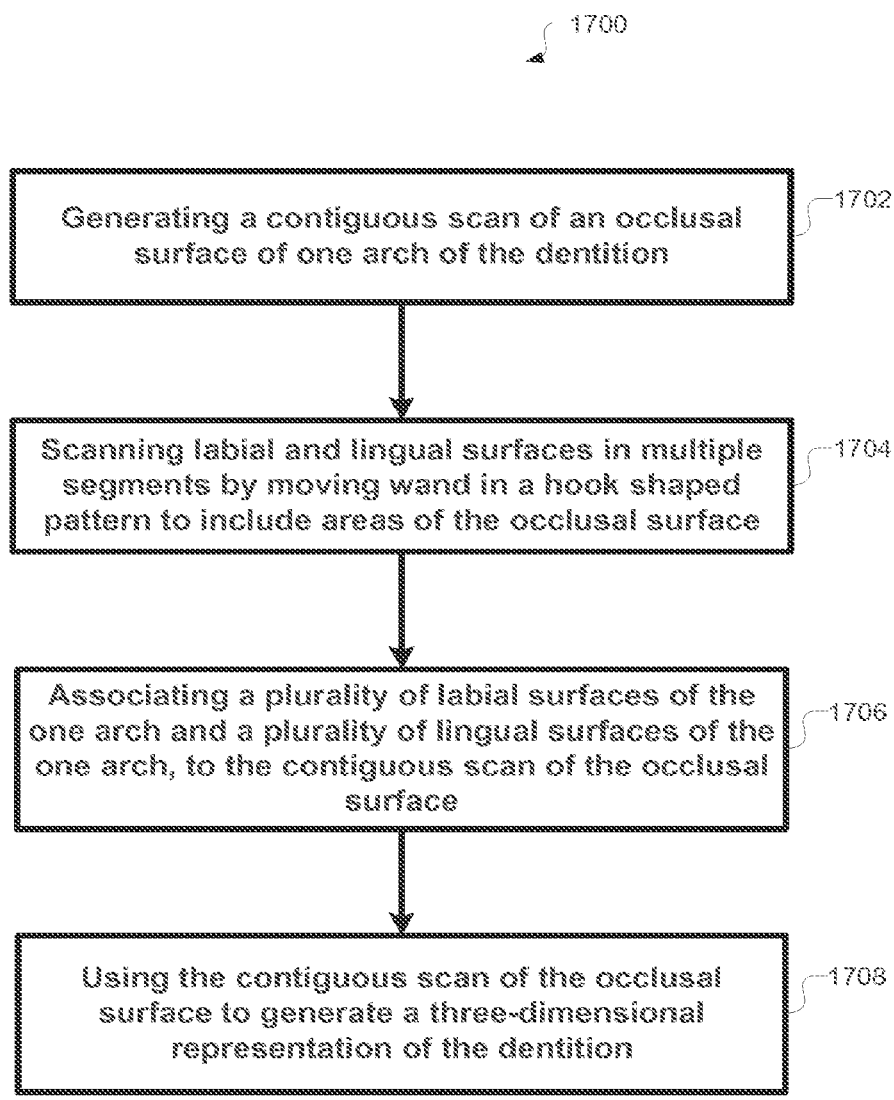
FIG. 17 illustrates a flowchart that shows how labial and lingual scans obtained by moving a wand in an exemplary pattern are associated with an occlusal backbone to display a three-dimensional reconstruction of the dental arch in accordance with certain embodiments.

FIG. 17 illustrates a flowchart 1700 that shows how labial and lingual scans obtained by moving a wand 108 in a hook shaped or some other pattern are associated with an occlusal backbone to display a three-dimensional reconstruction of the dental arch, in accordance with certain embodiments. The operations shown in FIG. 17 may be performed via the scanning and surface reconstruction application 110 that executes operations on the processor 104 of the intra-oral imaging system 102. In certain alternative embodiments, the operations shown in FIG. 17 may be performed in one or more computational devices that are external to the intra-oral imaging system 102.

Control starts at block 1702 in which a contiguous scan of an occlusal surface of one arch of a dentition is generated, where dentition refers to the arrangement of teeth n the oral cavity of a patient. Labial and lingual surfaces are scanned (at block 1704) in multiple segments by moving the wand 108 in a hook shaped or some other pattern to include areas of the occlusal surface.

Control proceeds to block 1706 in which the scanning and surface reconstruction application 110 associates a plurality of labial surfaces of the one arch and a plurality of lingual surfaces of the one arch, to the contiguous scan of the occlusal surface. The contiguous scan of the occlusal surface is therefore used to generate a three-dimensional representation of the dentition.

Figure 18:
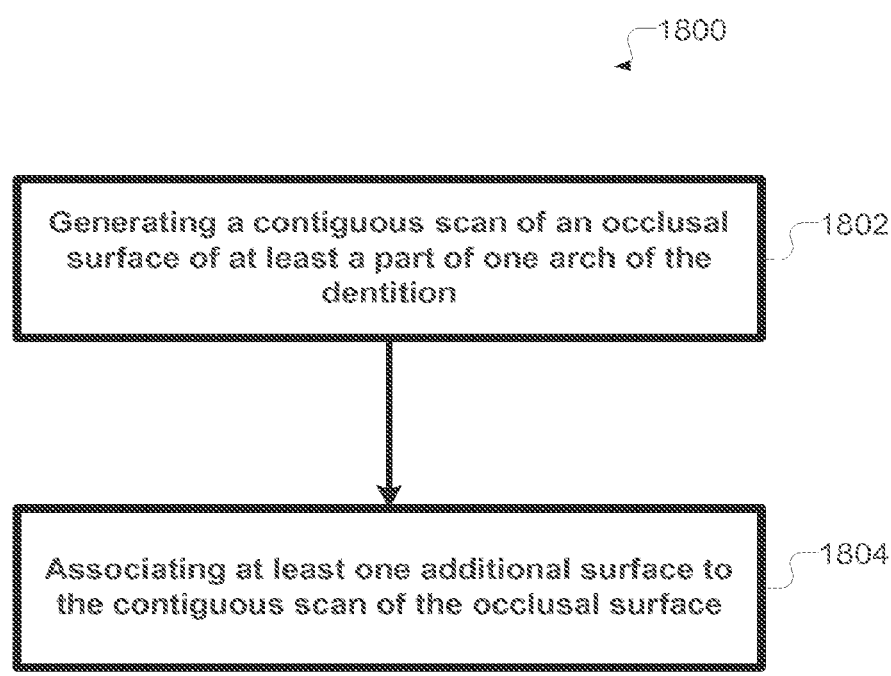
FIG. 18 illustrates a flowchart that shows how at least one additional surface is associated with a contiguous scan of an occlusal surface, in accordance with certain embodiments.

FIG. 18 illustrates a flowchart 1800 that shows how at least one additional surface is associated with a contiguous scan of an occlusal surface, in accordance with certain embodiments. The operations shown in FIG. 18 may be performed via the scanning and surface reconstruction application 110 that executes operations on the processor 104 of the intra-oral imaging system 102. In certain alternative embodiments, the operations shown in FIG. 18 may be performed in one or more computational devices that are external to the intra-oral imaging system 102.

Control starts at block 1802 in which a contiguous scan of an occlusal surface of at least a part of one arch of the dentition is generated. Control proceeds to block 1804 in which at least one additional surface is associated with the contiguous scan of the occlusal surface.

Figure 19:
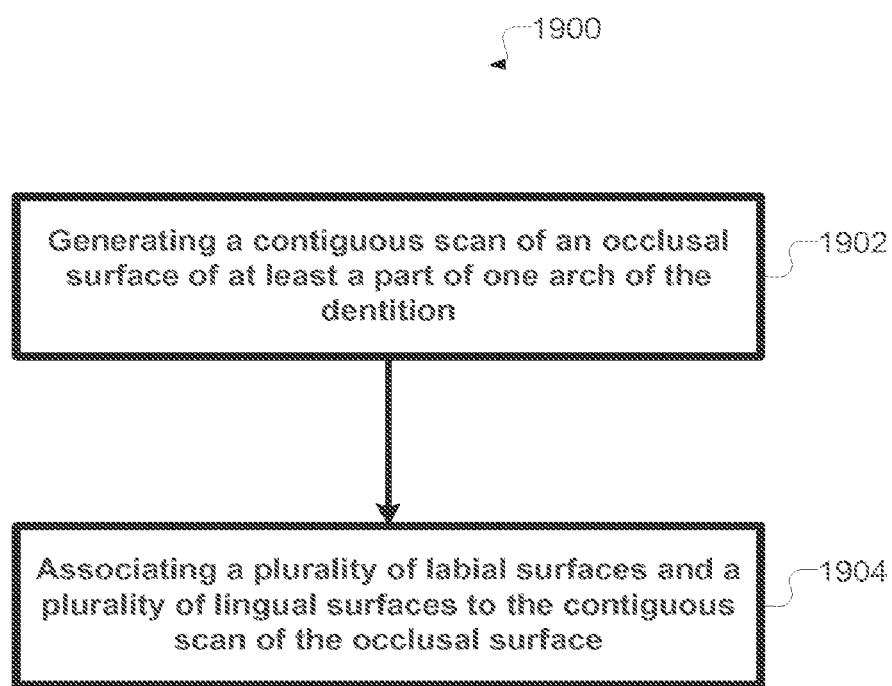
FIG. 19 illustrates a flowchart that shows how a plurality of labial and lingual surfaces are associated with a contiguous scan of an occlusal surface, in accordance with certain embodiments.

FIG. 19 illustrates a flowchart 1900 that shows how a plurality of labial and lingual surfaces are associated with a contiguous scan of an occlusal surface, in accordance with certain embodiments. The operations shown in FIG. 19 may be performed via the scanning and surface reconstruction application 110 that executes operations on the processor 104 of the intra-oral imaging system 102. In certain alternative embodiments, the operations shown in FIG. 19 may be performed in one or more computational devices that are external to the intra-oral imaging system 102.

Control starts at block 1902 in which a contiguous scan of an occlusal surface of at least a part of one arch of the dentition is generated. Control proceeds to block 1904 in which a plurality of labial surfaces and a plurality of lingual surfaces are associated with the contiguous scan of the occlusal surface.

Therefore, FIGS. 1-19 illustrate certain embodiments in which an occlusal backbone of a dental arch is generated from an contiguous occlusal scan, and then segments of labial and lingual surfaces are stitched to the occlusal backbone to generate a three-dimensional surface representation of the dental arch. The operations may be performed in real time via feature matching to generate a coarse match prior to using point clouds or other mechanisms for matching. Additionally, tongue, cheek, and lip data are removed to secure a more accurate occlusal backbone. The generation of the occlusal backbone prior to the labial and lingual scans facilitates the generation of a more accurate three dimensional representation of a dental arch in comparison to the situation in which the occlusal backbone is not generated. In certain embodiments, holes may be filled after the three-dimensional surface of the dental arch has been constructed. In other embodiments, image compression may be achieved during a statistical noise elimination process achieved by constructing a rough occlusal backbone with only those frames that overlap by around 50% or by some other percentage.

Additional Details of Embodiments

The operations described in the figures may be implemented as a method, apparatus or computer program product using techniques to produce software, firmware, hardware, or any combination thereof. Additionally, certain embodiments may take the form of a computer program product embodied in one or more computer readable storage medium(s) having computer readable program code embodied therein.

A computer readable storage medium may include an electronic, magnetic, optical, electromagnetic, or semiconductor system, apparatus, or device, or any suitable combination of the foregoing. The computer readable storage medium may also comprise an electrical connection having one or more wires, a portable computer diskette or disk, a hard disk, a random access memory (RAM), a read-only memory (ROM), an erasable programmable read-only memory (EPROM or Flash memory), a portable compact disc read-only memory (CD-ROM), an optical storage device, a magnetic storage device, etc. A computer readable storage medium may be any tangible medium that can contain, or store a program for use by or in connection with an instruction execution system, apparatus, or device.

A computer readable signal medium includes a propagated data signal pith computer readable program code embodied therein. A computer readable signal medium may be any computer readable medium that is not a computer readable storage medium and that can communicate, propagate, or transport a program for use by or in connection with an instruction execution system, apparatus, or device. The computer readable storage medium is different from the computer readable signal medium.

Computer program code for carrying out operations for aspects of the present invention may be written in any combination of one or more programming languages.

Aspects of the present invention are described below with reference to flowchart illustrations and/or block diagrams of methods, system and computer program products according to certain embodiments. At least certain operations that may have been illustrated in the figures show certain events occurring in a certain order. In alternative embodiments, certain operations may be performed in a different order, modified or removed. Additionally, operations may be added to the above described logic and still conform to the described embodiments. Further, operations described herein may occur sequentially or certain operations may be processed in parallel. Yet further, operations may be performed by a single processing unit or by distributed processing units. Computer program instructions can implement the blocks of the flowchart. These computer program instructions may be provided to a processor of a computer for execution.

Figure 20:
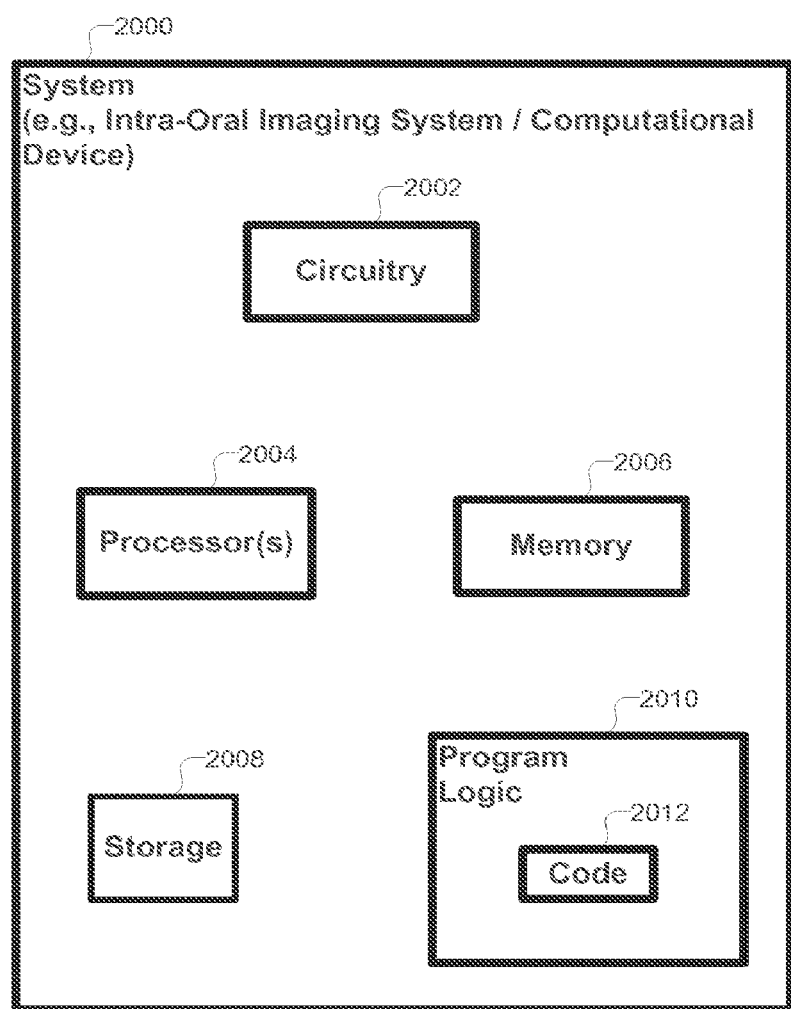
FIG. 20 illustrates a block diagram of a computational device that may correspond to the intra-oral imaging device shown in FIG. 1, in accordance with certain embodiments.

FIG. 20 illustrates a block diagram that shows certain elements that may be included in a computational device 2000, where in the computational device 2000 may be the infra-oral imaging system 102, in accordance with certain embodiments. The system 2000 may include a circuitry 2002 that may in certain embodiments include at least a processor 2004. The processor 2004 may comprise any suitable processor known in the art, such as, an arithmetic logical unit, a central processing unit, a circuitry that perform operations, hardware that performs instructions of a computer program, a microprocessor, a parallel processor, an array processor, a vector processor, a transistorized central processing unit, a microcontroller, a logic circuitry, etc. Any device that manipulates digital information based on one or more operational instructions or in a predefined manner is an example of the processor 2004. The system 2000 may also include a memory 2006 (e.g., a volatile memory device), and storage 2008. The storage 2008 may include a non-volatile memory device (e.g., EEPROM. ROM, PROM. RAM, DRAM, SRAM, flash, firmware, programmable logic, etc.), magnetic disk drive, optical disk drive, tape drive, etc. The storage 2008 may comprise an internal storage device, an attached storage device and/or a network accessible storage device. The system 2000 may include a program logic 2010 including code 2012 that may be loaded into the memory 2006 and executed by the processor 2004 or circuitry 2002. In certain embodiments, the program logic 2010 including code 2012 may be stored in the storage 2008. In certain other embodiments, the program logic 2010 may be implemented in the circuitry 2002. Therefore, while FIG. 20 shows the program logic 2010 separately from the other elements, the program logic 2010 may be implemented in the memory 2006 and/or the circuitry 2002.

The terms "an embodiment", "embodiment", "embodiments", "the embodiment", "the embodiments". "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A system, for generating an intra-oral scan of a dentition, the system comprising:
a memory; and
a processor coupled to the memory, wherein the processor is configured to:
generate a contiguous scan of an occlusal surface of at least a part of one arch of the dentition,
remove image data of soft tissue from the contiguous scan of the occlusal surface based at least in part on an analysis of 3D data from the contiguous scan to distinguish between image data of the dentition and the image data of the soft tissue, wherein the soft tissue includes at least one selected from a group consisting of a tongue, a cheek, and a lip, and
associate a scan of at least one additional surface to the contiguous scan of the occlusal surface by
analyzing the scan data to identify a portion of the scan of the at least one additional surface that overlaps with a portion of the contiguous scan of the occlusal surface,
wherein the scan of the at least one additional surface includes a sequence of image frames including a plurality of image frames of the occlusal surface interspersed with a plurality of image frames of the at least one additional surface, and
determining a position of the scan of the at least one additional surface relative to the scan of the occlusal surface based on the identified overlapping portions,
wherein the processor is configured to generate the contiguous scan of the occlusal surface by capturing a plurality of partially overlapping image frames of the occlusal surface and stitching the overlapping image frames together to form a 3D model of the occlusal surface,
wherein the processor is configured to remove the image data of the soft tissue from the contiguous scan by removing the image data of the soft tissue from the overlapping image frames used to generate the occlusal scan, and
wherein the processor is further configured to update the contiguous scan of the occlusal surface by restitching the overlapping image frames together after removing the image data of the soft tissue to form an updated 3D model of the occlusal surface.

2. The system of claim 1, wherein the processor is further configured to associate a plurality of scans of additional surfaces to the contiguous scan of the occlusal surface, wherein the plurality of scans of the additional surfaces includes a plurality of scans of labial surfaces and a plurality of scans of lingual surfaces.

3. The system of claim 1, wherein the plurality of image frames of the occlusal surface from the scan of the at least one additional surface each overlap with the contiguous scan of the occlusal surface,
wherein the plurality of images frames of the at least on additional surface includes image frames of a labial or lingual surface, and
wherein the processor is configured to use the plurality of image frames of the occlusal surface that is included in the scan of the at least one additional surface to determine a position of the image frames of the labial or lingual surface relative to the contiguous scan of the occlusal surface.

4. The system of claim 2, wherein the occlusal surface is imaged prior to the plurality of labial and lingual surfaces, and wherein the processor is further configured to display in real-time a three-dimensional representation of the dentition as the plurality of labial and lingual surfaces are imaged.

5. The system of claim 4, wherein the processor is configured to display in real-time the three-dimensional representation of the dentition by performing a coarse matching by matching features as the plurality of labial and lingual surfaces are imaged, and
wherein the processor is further configured to generate a three-dimensional reconstruction of the dentition based on a point cloud alignment after the plurality of labial and lingual surfaces are all imaged.

6. The system of claim 1, wherein the processor is further configured to generate an occlusal backbone by matching selected frames of the contiguous scan of the occlusal surface that have an overlap based on an analysis of data.

7. The system of claim 6, wherein the processor is configured to detect the overlap based on noise characteristics of the data.

8. The system of claim 1, further comprising:
a projector that projects interferometric fringes on an occlusal surface of at least a part of one arch of the dentition primarily along an anterior-posterior direction; and
an imaging sensor that is used to view the interferometric fringes,
wherein the processor is further configured to generate the contiguous scan of the occlusal surface based on the interferometric fringes sensed by the imaging sensor.

9. The system of claim 1, wherein the processor is configured to remove the image data of soft tissue from the contiguous scan of the occlusal surface based at least in part on the analysis of 3D data from the contiguous scan by distinguishing between the image data of the dentition and the image data of the soft tissue based at least in part on a comparison of surface normals of 3D structures in the contiguous scan.

10. A computer readable storage medium for generating an intra-oral scan of a dentition, wherein code stored in the computer readable storage medium, when executed by a processor, causes a system to:
generate a contiguous scan of an occlusal surface of at least a part of one arch of the dentition by capturing a plurality of partially overlapping image frames of the occlusal surface and stitching the overlapping image frames together to form a 3D model of the occlusal surface;
remove image data of soft tissue from the overlapping image frames used to generate the occlusal scan based at least in part on an analysis of 3D data from the contiguous scan to distinguish between image data of the dentition and the image data of the soft tissue, wherein the soft tissue includes at least one selected from a group consisting of a tongue, a cheek, and a lip;
update the contiguous scan of the occlusal surface by restitching the overlapping image frames together after removing the image data of the soft tissue to form an updated 3D model of the occlusal surface; and
associate a scan of at least one additional surface to the contiguous scan of the occlusal surface by
analyzing the scan data to identify a portion of the scan of the at least one additional surface that overlaps with a portion of the contiguous scan of the occlusal surface, wherein the scan data includes a sequence of image frames including a plurality of image frames of the occlusal surface interspersed with a plurality of image frames of the at least one additional surface, and determining a position of the scan of the at least one additional surface relative to the scan of the occlusal surface based on the identified overlapping portions.

11. The computer readable storage medium of claim 10, wherein the code, when executed by the processor, further causes the system to associate a plurality of scans of additional surfaces to the contiguous scan of the occlusal surface, wherein the plurality of scans of the additional surfaces includes a plurality of scans of labial surfaces and a plurality of scans of lingual surfaces.

12. The computer readable storage medium of claim 11, wherein the occlusal surface is imaged prior to the plurality of labial and lingual surfaces, and wherein the code, when executed by the processor, causes the system to display in real-time a three-dimensional representation of the dentition as the plurality of labial and lingual surfaces are imaged.

13. The computer readable storage medium of claim 12, wherein the code, when executed by the processor, causes the system to display in real-time the three-dimensional representation of the dentition by performing a coarse matching by matching features as the plurality of labial and lingual surfaces are imaged, and wherein the code, when executed by the processor, further causes the system to generate a three-dimensional reconstruction of the dentition based on a point cloud alignment after the plurality of labial and lingual surfaces are all imaged.

14. The computer readable storage medium of claim 10, wherein the plurality of image frames of the occlusal surface from the scan of the at least one additional surface each overlap with the contiguous scan of the occlusal surface, wherein the plurality of image frames of the at least one additional surface includes image frames of a labial or lingual surface, and wherein the code, when executed by the processor, causes the system to use the plurality of image frames of the occlusal surface that is included in the scan of the at least one additional surface to determine a position of the image frames of the labial or lingual surface relative to the contiguous scan of the occlusal surface.

15. The computer readable storage medium of claim 10, wherein the code, when executed by the processor, further causes the system to generate an occlusal backbone by matching selected frames of the contiguous scan of the occlusal surface that have an overlap based on an analysis of data.

16. The computer readable storage medium of claim 15, wherein the code, when executed by the processor, further causes the system to detect the overlap based on noise characteristics of the data.

17. The computer readable storage medium of claim 15, wherein the occlusal backbone is a first occlusal backbone, and wherein the code, when executed by the processor, further causes the system to generate a second occlusal backbone that is more accurate than the first occlusal backbone by linking other frames that are different from the selected frames to the first occlusal backbone.

18. The computer readable storage medium of claim 17, wherein the code, when executed by the processor, causes the system to remove the image data of the soft tissue from the contiguous scan of the occlusal surface by generating a third occlusal backbone by removing, from the second occlusal backbone, areas representing the soft tissue.

19. The computer readable storage medium of claim 18, wherein the code, when executed by the processor, causes the system to remove the image data of the soft tissue based at least in part on the analysis of 3D data from the contiguous scan by removing the image data of the soft tissue based at least in part on the analysis of the 3D data and at least one selected from a group consisting of a difference in color and a difference in rigidity properties.

20. The computer readable storage medium of claim 10, wherein the code stored in the computer readable storage medium, when executed by the processor, cause the system to remove the image data of soft tissue from the contiguous scan of the occlusal surface based at least in part on the analysis of 3D data from the contiguous scan by distinguishing between the image data of the dentition and the image data of the soft tissue based at least in part on a comparison of surface normals of 3D structures in the contiguous scan.

* * * * *